(12) United States Patent
Uhlmann et al.

(10) Patent No.: US 7,410,774 B1
(45) Date of Patent: Aug. 12, 2008

(54) COMPOUNDS MODULATING SISTER CHROMATID SEPARATION AND METHOD FOR IDENTIFYING SAME

(75) Inventors: Frank Uhlmann, Vienna (AT); Kim Nasmyth, Vienna (AT); Jan-Michael Peters, Korneuburg (AT); Irene Waizenegger, Wien (AT); Sara Buonomo, Vienna (AT); Rosemary Clyne, Vienna (AT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 09/500,991

(22) Filed: Feb. 15, 2000

Related U.S. Application Data

(60) Provisional application No. 60/126,767, filed on Mar. 29, 1999.

(30) Foreign Application Priority Data

Feb. 15, 1999 (EP) .................................. 99102962

(51) Int. Cl.
    C12Q 1/00    (2006.01)
    C12Q 1/37    (2006.01)
    C12N 9/00    (2006.01)
    C12N 9/50    (2006.01)
    C12N 9/64    (2006.01)
    C07K 1/00    (2006.01)

(52) U.S. Cl. .............................. 435/23; 435/4; 435/183; 435/219; 435/226; 530/350

(58) Field of Classification Search ..................... 435/4, 435/23, 183, 219, 226; 530/300, 350; 500/300
See application file for complete search history.

(56) References Cited

FOREIGN PATENT DOCUMENTS

| EP | 1227160 A1 * | 7/2002 |
|----|---|---|
| WO | WO 95/15749 A1 | 6/1995 |
| WO | WO 98/27994 A1 | 7/1998 |
| WO | WO 98/49190 A2 | 11/1998 |

OTHER PUBLICATIONS

Nagase et al. DNA Res. Feb. 29, 1996;3(1):17-24.*
Waizenegger et al. Cell. Oct. 27, 2000;103(3):399-410.*
Nomura et al. (DNA Res. 1994; 1(5):223-9.*
Sumara et al. J Cell Biol. Nov. 13, 2000;151(4):749-61.*
Hauf et al. Science. Aug. 17, 2001;293(5533):1320-3.*
Ambrose, W.P. et al., "Detection System for Reaction-Rate Analysis in a Low-Volume Proteinase-Inhibition Assay," *Analyt. Biochem.* 263:150-157 (Oct. 1998).
Brown, A.M. et al., "Biotinylated and Cysteine-Modified Peptides as Useful Reagents for Studying the Inhibition of Cathepsin G," *Analyt. Biochem.* 217:139-147 (1994).

Cai, J. et al., "Reconstitution of human replication factor C from its five subunits in baculovirus-infected insect cells," *Proc. Natl. Acad. Sci. USA* 93:12896-12901 (1996).
Cerratani, M. et al., "A High-Throughout Radiometric Assay for Hepatitis C Virus NS3 Protease," *Analyt. Biochem.* 266:192-197 (Jan. 1999).
Ciosk, R. et al., "An ESP1/PDS1 Complex Regulates Loss of Sister Chromatid Cohesion at the Metaphase to Anaphase Transition in Yeast," *Cell* 93:1067-1076 (Jun. 1998).
Cohen-Fix, O. et al., "Anaphase initiation in *Saccharomyces cerevisiae* is controlled by the APC-dependent degradation of the anaphase inhibitor Pds1p," *Genes & Devel.* 10:3081-3093 (1996).
Dominguez, A. et al., "*hpttg*, a human homologue of rat *pttg*, is overexpressed in hematopoietic neoplasms. Evidence for a transcriptional activation function of hPTTG," *Oncogene* 17:2187-2193 (Oct. 1998).
Dougherty, W. et al., "Molecular Genetic Analysis of a Plant Virus Polyprotein Cleavage Site: A Model," *Virology* 171:356-364 (1989).
Epstein, C.B., and Cross, F.R., "*CLB5*: a novel B cyclin from budding yeast with a role in S phase," *Genes & Devel.* 6:1695-1706 (1992).
Faleiro, L. et al., "Multiple species of CPP32 and Mch2 are the major active caspases present in apoptotic cells," *EMBO J.* 16:2271-2281 (1997).
Funabiki, H. et al., "Cut2 proteolysis required for sister-chromatid separation in fission yeast," *Nature* 381:438-441 (1996).
Gershkovich, A.A., and Kholodovych, V.V., "Fluorogenic substrates for proteases based on intramolecular fluorescence energy transfer (IFETS)," *J. Biochem. Biophys. Methods* 33:135-162 (1996).
Gietz, R.D. and Sugino, A., "New yeast- *Escherichia coli* shuttle vectors constructed with in vitro mutagenized yeast genes lacking six-base pair restriction sites," *Gene* 74:527-534 (1988).
Gray, N.M. et al., "Discovery and Analysis of a Series of $C_2$-Symmetric HIV-1 Proteinase Inhibitors Derived from Penicillin," *Analyt. Biochem.* 216:89-96 (1994).
Hayden, J.H. et al., "Kinetochores Capture Astral Microtubules During Chromosome Attachment to the Mitotic Spindle: Direct Visualization in Live Newt Lung Cells," *J. Cell Biol.* 111:1039-1045 (1990).
Jolley, M.E., "Fluorescence Polarization Assays for the Detection of Proteases and Their Inhibitors," *J. Biomol. Screening* 1:33-38 (1996).
Kerrebrock, A.W. et al., "Mei-S332, a *Drosophila* Protein Required for Sister-Chromatoid Cohesion, Can Localize to Meiotic Centromere Regions," *Cell* 83:247-256 (1995).
Klein, F. et al., "A Central Role for Cohesins in Sister Chromatid Cohesion, Formation of Axial Elements, and Recombination during Yeast Meiosis," *Cell* 98:91-103 (Jul. 1999).

(Continued)

*Primary Examiner*—Tekchand Saidha
*Assistant Examiner*—Christian L Fronda
(74) *Attorney, Agent, or Firm*—Sterne, Kessler, Goldstein & Fox P.L.L.C.

(57) ABSTRACT

Method for identifying compounds that interfere with or modulate sister chromatid separation in animal or plant cells by modulating a protease with separin-like cysteine endopeptidase activity. Inhibitors of separin activity are useful in cancer therapy, to prevent birth defects and to increase ploidy in plants.

12 Claims, 24 Drawing Sheets

OTHER PUBLICATIONS

Kramer, E.R. et al., "Activation of the human anaphase-promoting complex by proteins of the CDC20/Fizzy family," *Curr. Biol. 8*:1207-1210 (Oct. 1998).

Levine, L.M. et al., "Measurement of Specific Protease Activity Utilizing Fluorescence Polarization, " *Analyt. Biochem. 247*:83-88 (1997).

Liang, C. and Stillman, B., "Persistent initiation of DNA replication and chromatin-bound MCM proteins during the cell cycle in *cdc6* mutants," *Genes & Devel. 11*:3375-3386 (1997).

Lim H.H. et al., "Cdc20 is essential for the cyclosome-mediated proteolysis of both Pds1 and Clb2 during M phase in budding yeast," *Curr. Biol. 8*:231-234 (Feb. 1998).

Losada, A. et al., "Identification of *Xenopus* SMC protein complexes required for sister chromatid cohesion," *Genes & Devel. 12*:1986-1997 (Jul. 1998).

Matayoshi, E.D. et al., "Novel Fluorogenic Substrates for Assaying Retroviral Proteases by Resonance Energy Transfer," *Science 247*:954-958 (1990).

McGrew. J.T. et al., "Requirement for *ESP1* in the Nuclear Division of *Saccharomyces cerevisiae*," *Mol. Biol. Cell 3*:1443-1454 (1992).

McKay, M.J. et al., "Sequence Conservation of the *rad21 Schizosaccharomyces pombe* DNA Double-Strand Break Repair Gene in Human and Mouse," *Genomics 36*:305-315 (1996).

Merdes, A. and De Mey, J., "The mechanism of kinetochore-spindle attachment and polewards movement analyzed in $PtK_2$ cells at the prophase-prometaphase transition," *Eur. J. Cell Biol. 53*:313-325 (1990).

Michaelis, C. et al., "Cohesions: Chromosomal Proteins that Prevent Premature Separation of Sister Chromatids," *Cell 91*:35-45 (1997).

Miyazaki, W.Y. and Orr-Weaver, T.L., "Sister-Chromatid Cohesion in Mitosis and Meiosis," *Annu. Rev. Genet. 28*:167-187 (1994).

Moore, D.P. et al., "The Cohesion Protein MEI-S332 Localizes to Condensed Meiotic and Mitotic Centromeres until Sister Chromatids Separate," *J. Cell Biol. 140*:1003-1012 (Mar. 1998).

Murray, A.W., "Cell Cycle Extracts," *Meth. Cell Biol. 36*:581-605 (1991).

Murray, M.G. et al., "Inactivation of a yeast transactivator by the fused HIV-1 proteinase: a simple assay for inhibitors of the viral enzyme activity," *Gene 134*:123-128 (1993).

Nagase, T. et al., "Prediction of the Coding Sequences of Unidentified Human Genes. V. The Coding Sequences of 40 New Genes (KIAA0161-KIAA0200) Deduced by Analysis of cDNA Clones from Human Cell Line KG-1," *DNA Res. 3*:17-24 (1996).

Nicholson, D.W. et al., "Identification and inhibition of the ICE/CED-3 protease necessary for mammalian apoptosis," *Nature 376*:37-43 (1995).

Peters, J.-M., "SCF and APC: the Yin and Yang of cell cycle regulated proteolysis," *Curr. Opin. Cell Biol. 10*:759-768 (Dec. 1998).

Rieder, C.L. and Salmon, E.D., "The vertebrate cell kinetochore and its roles during mitosis," *Trends in Cell Biol. 8*:310-318 (Aug. 1998).

Sarubbi, E. et al., "A high throughput assay for inhibitors of HIV-1 protease," *FEBS Lett. 279*:265-269 (1991).

Singh, J. et al., "Lead Development: Validation and Application of High Throughput Screening For Determination of Pharmacokinetic Parameters for Enzyme Inhibitors," *Bioorganic & Medicinal Chem. 4*:639-643 (1996).

Stebbins, J. and Debouck, C., "A Microtiter Colorimetric Assay for the HIV-1 Protease," *Analyt. Biochem. 248*:246-250 (1997).

Taliani, M. et al., "A Continuous Assay of Hepatitis C Virus Protease Based on Resonance Energy Transfer Depsipeptide Substrates," *Analyt. Biochem. 240*:60-67 (1996).

Uhlmann, F. and Nasmyth, K., "Cohesion between sister chromatids must be established during DNA replication," *Curr. Biol. 8*:1095-1101 (Sep. 1998).

Zou, H. et al., "Identification of a Vertebrate Sister-Chromatid Separation Inhibitor Involved in Transformation and Tumorigenesis," *Science 285*:418-422 (Jul. 1999).

Clark, D.A., et al., "Protease Inhibitors Suppress In Vitro Growth of Human Small Cell Lung Cancer," *Peptides 14*:1021-1028, Pergamon Press Ltd. (1993).

NCBI Entrez, GenBank Report, Accession No. D79987, from Nomura, N. (1995).

Uhlmann, F., et al., "Sister-chromatid separation at anaphase onset is promoted by cleavage of the cohesion subunit SCC1," *Nature 400*:37-42, Macmillan Journals Ltd. (Jul. 1999).

International Search Report for International Patent Application No. PCT/EP00/01183, mailed Jun. 29, 2000.

Pending U.S. Appl. No. 10/051,311, filed Jan. 22, 2002, Peters et al.

\* cited by examiner

Fig. 1 a
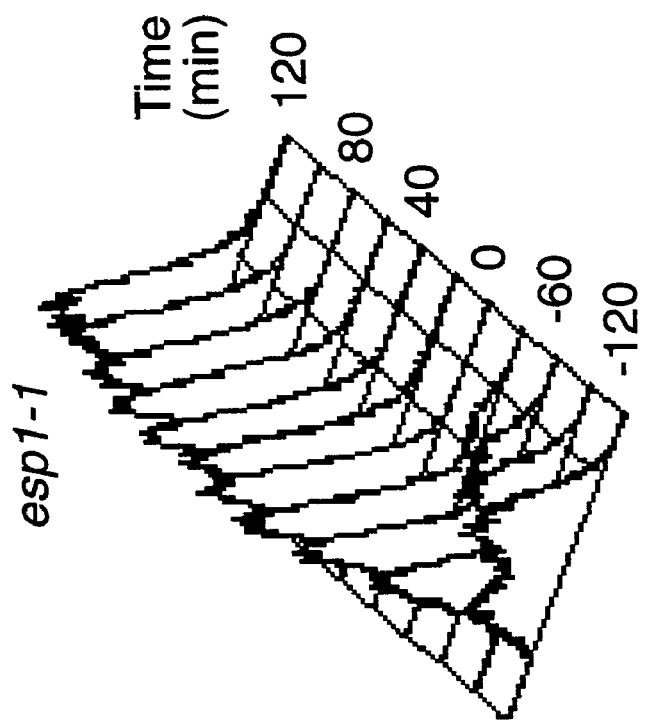
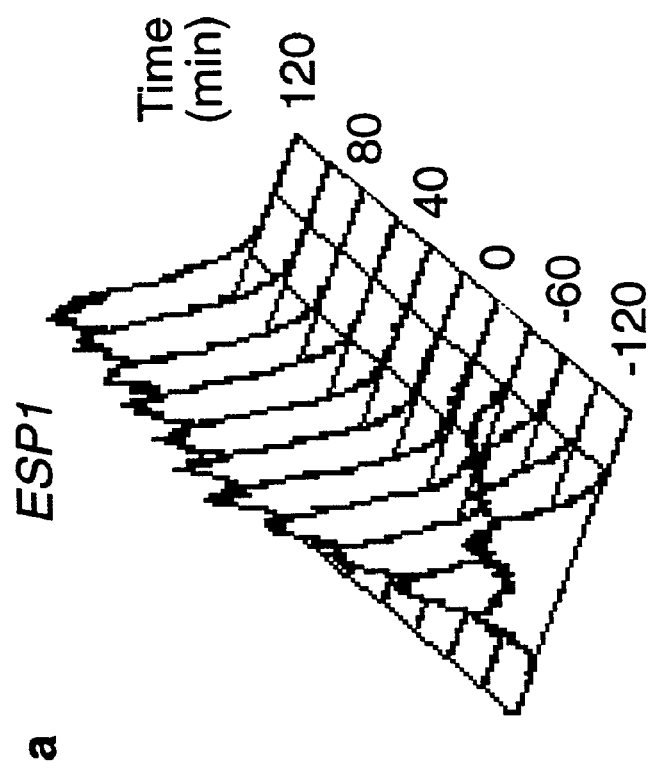

Fig. 3 a, b
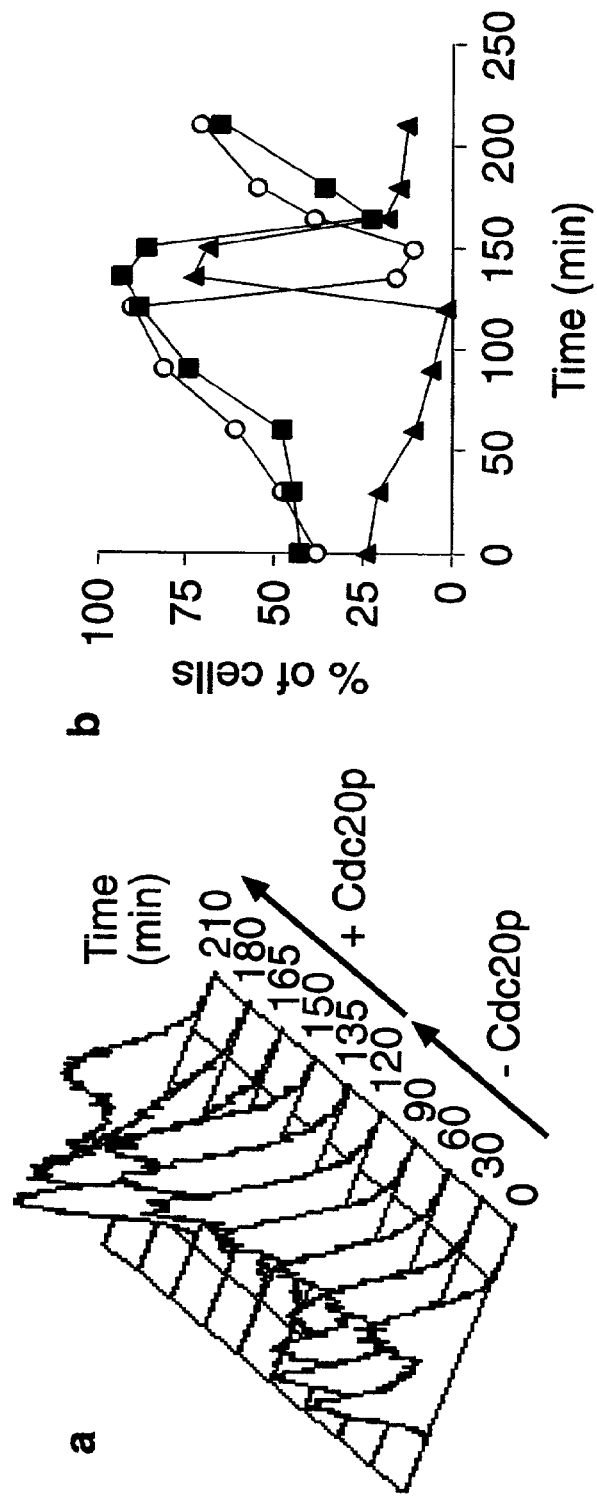

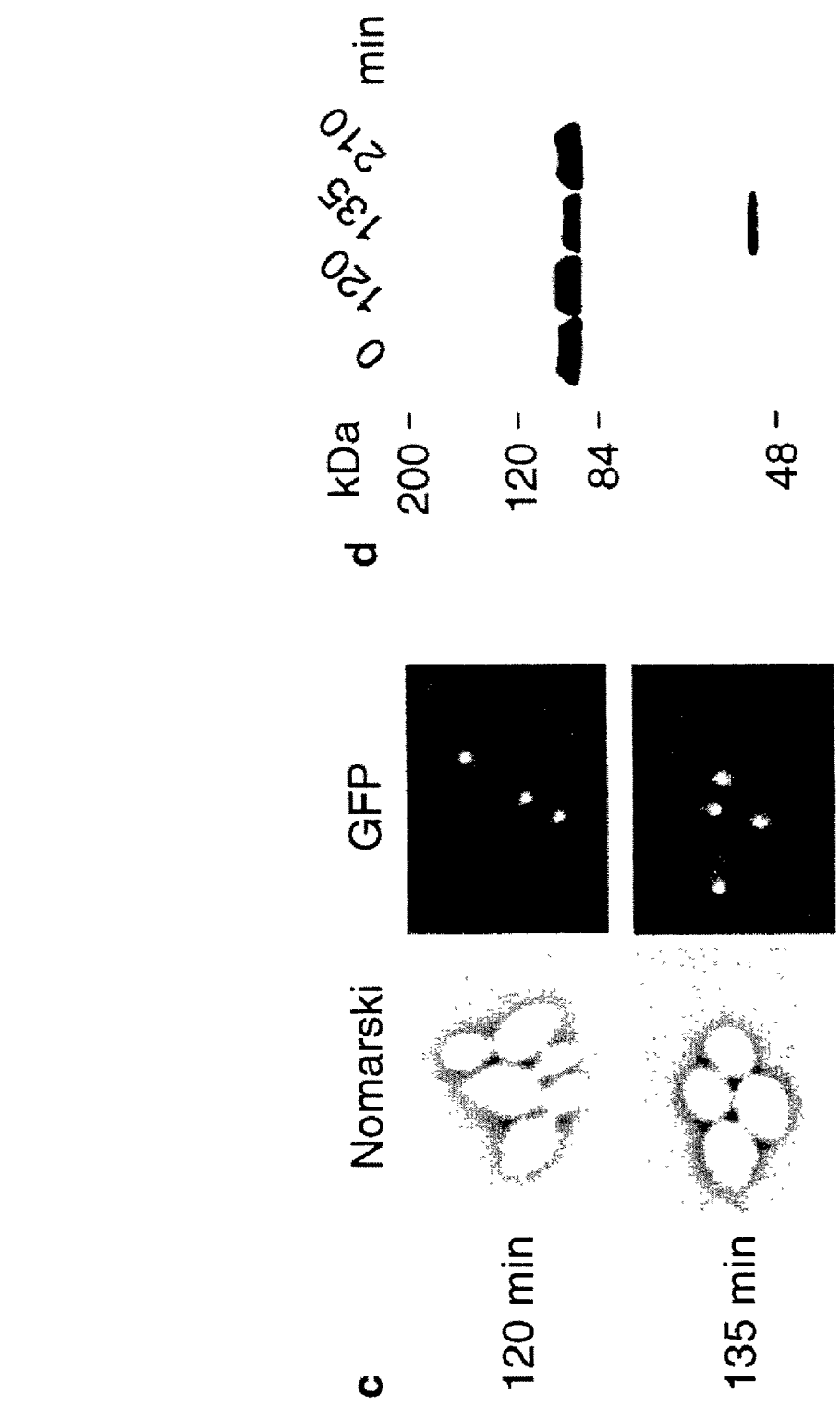
Fig. 3 c, d

Fig. 4 b, c
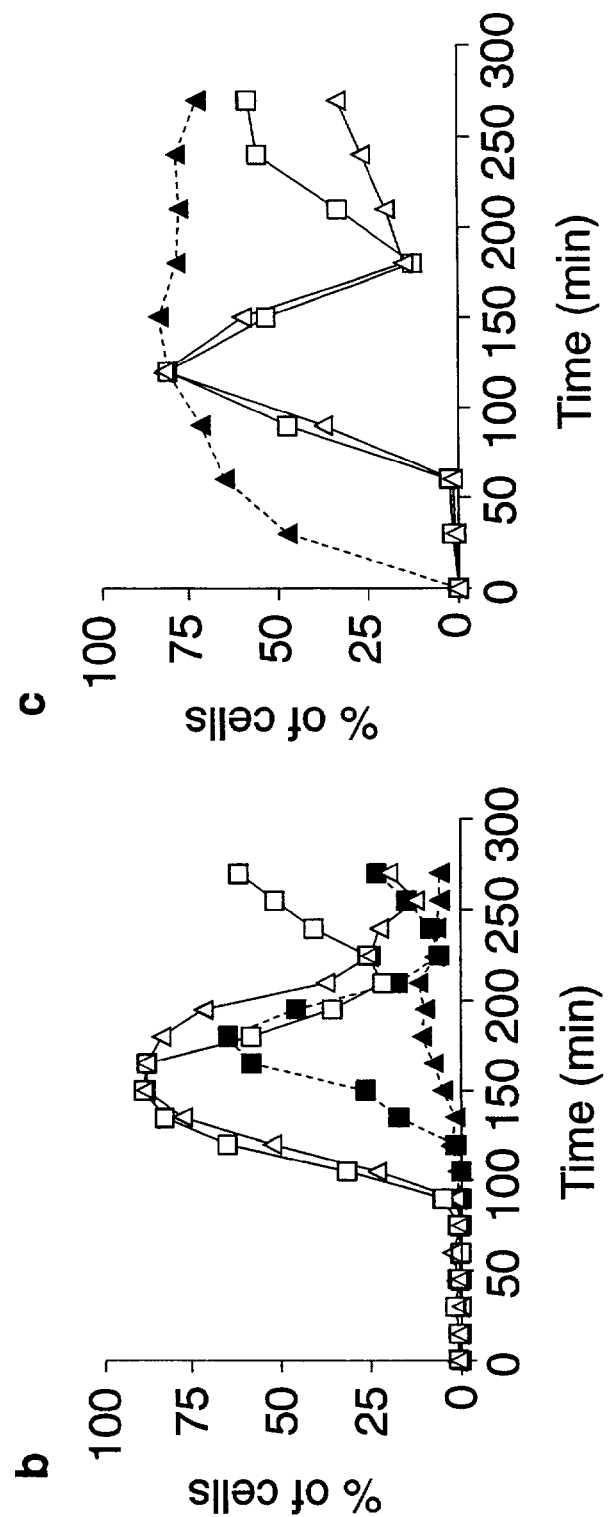

Figure 7
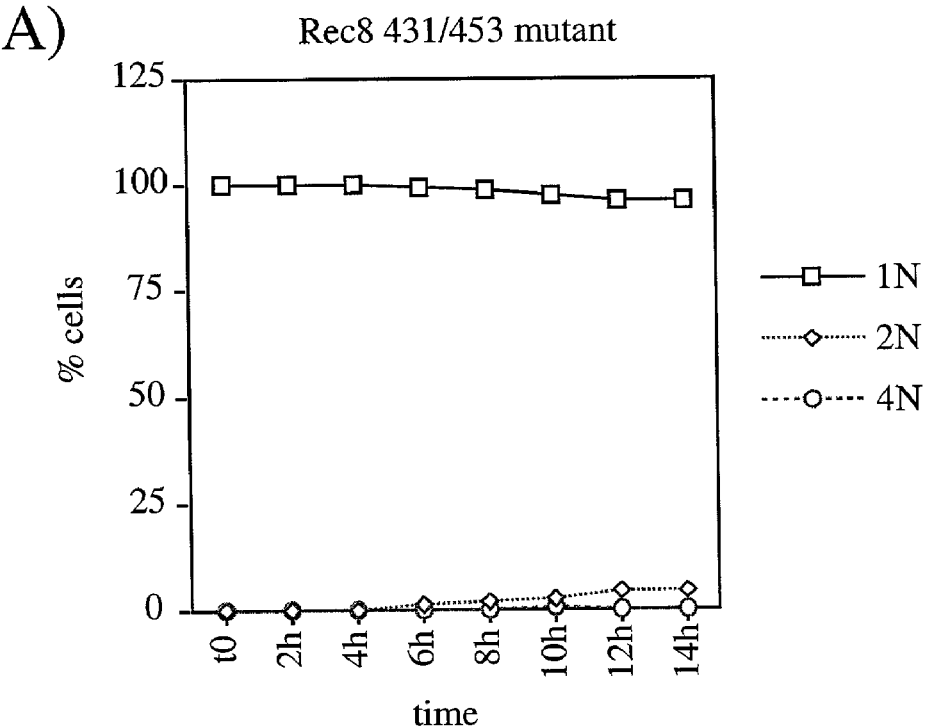
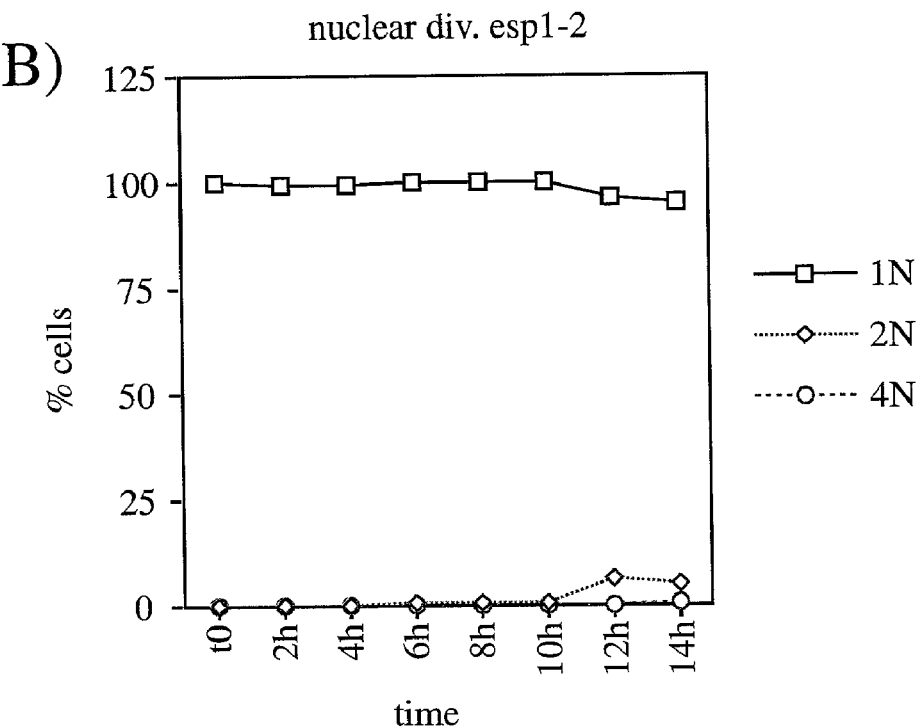

Fig. 14
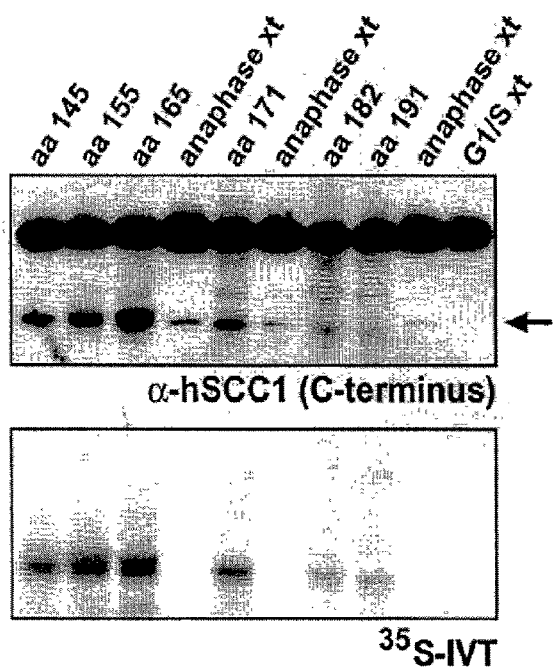
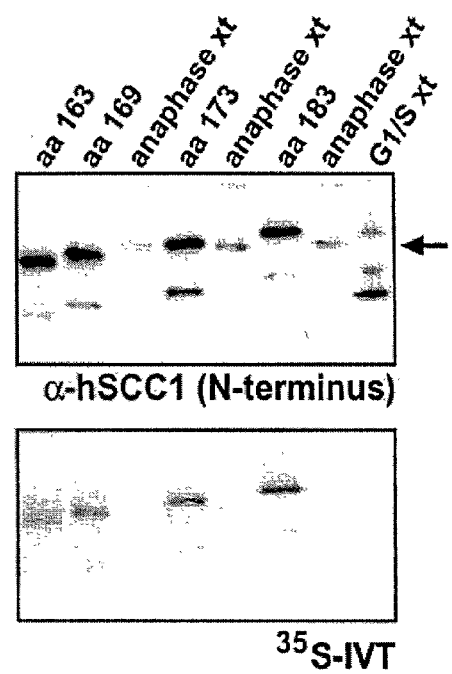

COMPOUNDS MODULATING SISTER CHROMATID SEPARATION AND METHOD FOR IDENTIFYING SAME

This application claims priority benefit to U.S. provisional appl. No. 60/126,767, filed Mar. 29, 1999.

The invention relates to compounds influencing mitosis and meiosis in eukaryotic cells and methods for identifying such compounds. In particular, the invention largely relates to the treatment and prevention of human conditions by modulating sister chromatid segregation.

During the process of cell division, sister chromatids are pulled to opposite halves of the cell by microtubules emanating from spindle poles at opposite sides of the cell. One set of microtubules inter-digitates with others emanating from the opposite pole. Their role is to keep (and drive) the two poles apart. Meanwhile, a second set of microtubules attaches to chromosomes via specialized structures called kinetochores and pulls them towards the poles. Sister chromatids segregate away from each other because their kinetochores attach to microtubules emanating from opposite poles (Rieder et al., 1998). Chromosomes are not mere passengers during this process. During metaphase, the tendency of microtubules to move sisters apart is counteracted by cohesion holding sisters together. Cohesion therefore generates the tension by which cells align sister chromatids on the metaphase plate. Were sisters to separate before spindle formation, it is difficult to imagine how cells could distinguish sisters from chromatids that were merely homologous. The sudden loss of cohesion, rather than an increase in the exertion of microtubules, is thought to trigger sister separation during anaphase (Miyazaki et al., 1994). Cohesion also prevents chromosomes from falling apart due to double strand breaks and facilitates their repair using recombination.

To avoid missegregation of chromosomes, anaphase must only be initiated after sister chromatids of each duplicated chromosome have attached to opposite poles of the mitotic spindle. Microtubules are thought to "find" kinetochores by a "search and capture" mechanism which cannot be completed simultaneously for all chromosomes (Hayden et al., 1990; Merdes and De Mey, 1990). Cells therefore possess regulatory mechanisms that delay sister chromatid separation until the last chromosome has achieved bipolar attachment. The dissolution of sister chromatid cohesion at the metaphase to anaphase transition is therefore a highly regulated step during the eukaryotic cell cycle.

Sister chromatid cohesion depends on a multi-subunit complex called cohesin (Losoda et al., 1998), which contains at least four subunits: Smc1p, Smc3p, Scc1p, and Scc3p, all of which are conserved between yeast and humans. It is likely, but not yet proven, that cohesin is a key constituent of the tether that holds sister chromatids together. The association between cohesin and chromosomes has recently been shown to depend on the Scc2 (Mis4) protein. Cohesion is established during DNA replication (Uhlmann and Nasmyth, 1998). It has been recently shown that the Eco1 (Ctf7) protein is required for the establishment of cohesion during S phase but unlike cohesin is not required to maintain cohesion during G2 and M phases. In yeast, cohesin remains tightly associated with chromosomes until metaphase; that is, it is present on chromosomes during their alignment during metaphase. In animal cells, however, the bulk of cohesin dissociates from chromosomes during prophase (Losada et al., 1998). It is unclear how much cohesin, if any, remains on chromosomes during metaphase. The nature of the link that holds sister chromatids together during metaphase in animal cells is therefore unclear. It could either involve a small fraction of cohesin that remains associated with chromosomes or some other protein complex.

In yeast, at least two of cohesin's subunits, Scc1p and Scc3p, suddenly disappear from chromosomes at precisely the point at which sister chromatids separate (Michaelis et al., 1997). This has led to the notion that a sudden change in the state of cohesin might trigger the onset of anaphase, at least in yeast. In Drosophila, the meiS332 protein, which binds to chromosomes during prometaphase, also disappears at the onset of anaphase. MeiS332 is required for sister chromatid cohesion during meiosis but not during mitosis (Moore et al., 1998; Kerrebrock et al., 1995). MeiS332 is probably not a cohesin subunit nor is it apparent whether homologous proteins exist in humans.

Both the dissociation of Scc1p from chromosomes and the separation of sister chromatids are dependent on a specialized sister separating protein (a separin) called Esp1p (Ciosk et al., 1998). Separins homologous to Esp1 exist in the fission yeast *Schizosaccharomyces pombe*, in the fungus *Aspergillus nidulans*, in the nematode worm *Caenorhabditis elegans*, the fruit fly *Drosophila melanogaster*, in the frog *Xenopus laevis*, in the plant *Arabidopsis thaliana*, and in man. This strongly suggests that separins have a fundamental role in chromosome segregation that is conserved between plants, fungi, and animals. Esp1 is tightly bound by an inhibitory protein called Pds1p whose destruction shortly before the metaphase to anaphase transition is triggered by ubiquitination mediated by the anaphase promoting complex (APC) (Cohen-Fix et al., 1996). The APC is large multi-subunit complex, most of whose subunits are conserved between yeast and humans. Together with activator proteins called Cdc20p and Cdh1p, it mediates the ubiquitination and thereby destruction of many different cell cycle proteins, including anaphase inhibitors like Pds1 and mitotic cyclins. Pds1 destruction is mediated by a form of the APC bound by the activator Cdc20. This form is called $APC^{Cdc20}$. (For a review, see Peters, 1998)

Proteins with similar properties to Pds1 have been found in fission yeast (Cut2p), in *Xenopus*, and in humans (Funabiki et al., 1996; Zou et al., 1999). The APC is essential for sister chromatid separation in most if not all eukaryotic organisms. In yeast, it is clear that its main role in promoting sister separation is to destroy Pds1, which liberates Esp1 and allows it to destroy sister chromatid cohesion, possibly by destroying the physical links between sisters mediated by cohesin.

It was an object of the invention to further eluciate the mechanism of sister chromatid separation.

In particular, it was an object of the invention to understand the mechanism by which Esp1p mediates the dissocation of Scc1p from chromosomes in the budding yeast in order to take advantage of this mechanism by using it as a target in human therapy, in particular of cancer therapy, and as a target in all other situations where modulation of sister chromatid separation is therapeutically or otherwise beneficial.

To solve the problem underlying the present invention, the following approach was taken:

The observation that the dissociation of Scc1p from chromosomes at the onset of anaphase is dependent on Esp1 suggested that Esp1 might either have a direct role in this process or that Esp1 might be indirectly involved by initiating a process that leads to Scc1p's dissociation. It was found in experiments of the present invention that Esp1 also prevents association of Scc1p with chromosomes during G1 (see Example 1), which strongly suggests that Esp1's role might be very direct. Scc1p is an unstable protein which is rapidly destroyed following its dissociation from chromosomes at the onset of anaphase and which must be re-synthesised during late G1 during the next cell cycle in order for cohesion to be established at the next round of DNA replication (Michaelis et al., 1997) It was found that Scc1p synthesised during G2 is also capable of binding to yeast chromosomes but that it fails to produce cohesion under these circumstances (Uhlmann and Nasmyth, 1998). However, it was noted that Scc1p synthesised during early G1 binds to chromosomes poorly, if at all. As shown in FIG. 1, inactivation of Esp1permits the efficient association between Scc1p and chromosomes during early G1. The implication is that Esp1 not only triggers Scc1p's dissocation from chromosomes at the onset of anaphase but also prevents Scc1p's stable association with chromosomes during the subsequent G1 period. This strongly suggests that Esp1 has a fairly direct role in controlling the association between Scc1p and chromosomes.

Starting from this finding, an assay was established by which Esp1 activity could be measured in vitro. A crude preparation of yeast chromatin isolated from cells arrested in a metaphase-like state by nocodazole, was incubated with a soluble extract prepared from cells over-producing Esp1 from the GAL promoter (FIG. 2). To detect Scc1p, cells were used whose Scc1 protein was tagged at its C-terminus with multiple HA or Myc epitopes, which can readily be detected with monoclonal antibodies. About 70% of the total Scc1p in nocodazole blocked cells is tightly associated with chromatin and is therefore present in the chromatin fraction that was used. Most of the Scc1p remains tightly associated with chromatin following incubation with an extract prepared from esp1-1 mutant cells but most disappears from the chromatin fraction upon incubation with extracts containing high levels of wild type Esp1 protein. Somewhat surprisingly, the Scc1p protein induced to dissociate from chromatin by Esp1 appeared in the "soluble" supernatant fraction as a cleaved product. The C-terminal fragments of this cleavage were detected by using as a substrate a C-terminally tagged Scc1 protein and N-terminal fragments using as substrate an N-terminally tagged Scc1 protein. The sizes of these cleavage products suggested that Esp1 induces one or more specific cleavages of Scc1p within a 10 kd interval. This Esp1-dependent cleavage was inhibited by the addition of reticulate lysate that had translated Pds1 but not by an otherwise identical lysate that had translated an unrelated control protein. The Esp1 activity detected by the cleavage assay is therefore inhibited by Pds1, which demonstrates directly, for the first time, that Pds1 is indeed an inhibitor of Esp1p.

To address whether Esp1 induced cleavage of Scc1p also occurs in vivo at the onset of anaphase, a yeast strain was constructed in which expression of the APC activator Cdc20p is under control of the galactose inducible GAL1-10 promoter. The strain also expressed an Scc1 protein tagged at its C-terminus with multiple HA or myc epitopes. Cells from this strain were arrested in metaphase by incubation in galactose free medium and then induced to embark on anaphase highly synchronously by the addition of galactose. FIG. 3 shows that sister chromatids separate in most cells within 15 minutes and that Scc1p dissociates from chromosomes with similar if not identical kinetics. A low level of an Scc1 cleavage product was detected that is identical to that seen in vitro in cycling cells but none in cells arrested in metaphase. The cleavage product suddenly appeared upon induction with galactose with kinetics that were similar if not identical to the separation of sister chromatids and dissocation of Scc1p from chromosomes. To establish whether this in vivo cleavage was dependent on Esp1 activity the extent of Scc1p cleavage in wild type and esp1-1 mutants when released from cdc20 arrest at 35.5° C. was compared (the restrictive temperature for esp1-1). The extent of Scc1p cleavage was greatly reduced in the esp1-1 mutant. It was concluded that Esp1 promotes the cleavage of Scc1p and its dissociation from chromosomes both in vivo and in vitro.

To address whether cleavage of Scc1 mediated by Esp1 is important either for sister chromatid separation or for Scc1p's dissociation from chromosomes, the cleavage site was mapped in order that it could then be mutated. An epitope tagged Scc1p protein from cells that had been stimulated to undergo anaphase by induction of Cdc20 expression was immunoprecipiated and the immunoprecipitated proteins were separated on SDS page. A short stretch of N-terminal amino acid sequence from the C-terminal cleavage fragment was then determined by Edman degradation. This showed that cleavage in vivo had occurred between a pair of arginines at positions 268 and 269. The N-terminal of these arginine residues was then mutated to aspartic acid and an HA tagged version then was expressed from the GAL1-10 promoter in yeast cells whose endogenous Scc1 protein was myc tagged. Galactose induced expression of this single mutant protein had little effect on cell proliferation. To establish whether the mutation had indeed abolished cleavage, chromatin from cells expressing the mutant protein was isolated and used as a substrate in the Esp1 assay. This showed that cleavage at site 268 was indeed eliminated by the aspartic acid mutation. However, the mutated protein was still cleaved in an Esp1-dependent manner. The C-terminal cleavage product from the mutant protein was about 10 kDa longer than that from wild type. The interpretation of these results is that Scc1p is actually cleaved at two sites approximately 10 kDa apart. Cleavage at the more C-terminal site is highly efficient, which is why C-terminal tagged proteins cleaved only at the more N-terminal site were rarely detected.

To identify the second cleavage site, sequences within Scc1p which are similar in sequence to those surrounding the known C-terminal cleavage site were looked for. A 5 out of 7 amino acid match at position 180 found. Furthermore, the distance between this potential site and the known cleavage site is consistent with the greater length of the cleavage product generated in vitro from protein whose C-terminal site (R268) had been mutated. The matching sequence also contained a pair of arginines and therefore the more N-terminal arginine was mutated to aspartic acid. Next the effect of expressing HA tagged versions of wild type Scc1p, both single mutant proteins, and the double mutant protein from the GALL promoter in yeast was compared. As a host for these studies a strain was used whose endogenous Scc1p was myc tagged. Neither wild type nor either single mutant blocked cell proliferation but expression of the double mutant protein was lethal. Chromatin from cells transiently expressing these proteins was prepared and it was shown that HA tagged double mutant protein was no longer cleaved when incubated in Esp1-containing extracts while the myc tagged wild type protein was efficiently cleaved.

To investigate why cells expressing a non-cleavable Scc1p protein (the R180D R268D double mutant) cannot proliferate, centrifugal elutriation was used to isolate G1 cells from a culture growing in the absence of galactose, which were then incubated in the presence and absence of galactose (FIG. 4). In order to minimize the duration of mutant protein expression, the cells grown in the presence of galactose were transferred to glucose containing medium after most cells had replicated their DNA (at 135 min). In the absence of galactose, sister separation and dissociation from chromosomes of endogenous myc tagged Scc1p occurred simultaneously, approximately 60 min after DNA replication. Transient expression of double mutant protein greatly reduced sister chromatid separation (FIG. 4b) but did not affect dissociation of endogenous myc tagged wild type protein (FIGS. 4c and d). Furthermore, the mutant protein remained tightly associated with chromosomes long after the endogenous wild type protein had disappeared. Expression of the mutant protein did not greatly delay cell cycle progression and most cells underwent cytokinesis, producing progeny with low (0-0.5C) amounts of DNA and cells with less than a 2C DNA content (FIG. 4a). The dissociation from chromosomes of wild type protein on schedule shows that the lack of sister separation in cells expressing non-cleavable Scc1p is not due to a lack of Esp1 activity. Collectively, the data obtained imply that cleavage of Scc1p at one of two sites is necessary both for sister chromatid separation and for dissociation of Scc1p from chromosomes.

From the obtained results it can be concluded that cohesin directly mediates the link between sister chromatids that is established during DNA replication and is maintained until metaphase. It can be further concluded that Esp1's activation by proteolysis of Pds1 (and by as yet to be identified other mechanisms) generates an activity inside cells that cleaves the Scc1p subunit of cohesin and that this event both destroys sister chromatid cohesion and causes Scc1p and possibly other cohesin subunits to dissociate from chromosomes.

From the above results it is clear that sister chromatid separation depends on cleavage of chromosome-bound Scc1 by an Esp1-dependent proteolytic activity that appears in cells at the onset of anaphase. It was next asked whether Scc1 as an isolated protein (rather than in the chromosomal context) can also serve as a substrate for the Esp1-dependent cleavage reaction. FIG. 5 describes the purification of recombinant Scc1 after over-expression in insect cells infected with a recombinant baculovirus. Scc1 was purified either from an asynchronously growing population of infected insect cells (FIG. 5a, lanes 1-4) or from infected insect cells that had been treated with the phosphatase inhibitor okadaic acid. Treatment with okadaic acid induces a metaphase-like state within the insect cells as a consequence of which Scc1 is obtained in a mitotically phosphorylated form (FIG. 5a, lane 5). Scc1 in yeast appears also phosphorylated in a mitosis specific manner. These Scc1 fractions, that were more than 90% pure as judged by SDS-PAGE followed by staining of the gel with Coomassie brilliant blue, were then used in the Scc1 cleavage assay as described above (FIG. 5b). Both unphosphorylated and phosphorylated purified Scc1 were cleaved in an Esp1-dependent manner in vitro, however, the efficiency of cleavage was much greater when Scc1 was in the mitotically phosphorylated state. From this experiment it was concluded that isolated Scc1 which is neither part of the cohesin compex nor bound to chromosomes is a substrate for cleavage by Esp1, at least if it is in its mitotically phosphorylated state.

It was then addressed, whether Esp1 is itself the protease that cleaves Scc1. Inhibitor studies showed that the in vitro cleavage activity could be inhibited by N-ethyl maleimide an inhibitor specific for proteases using a catalytic cysteine residue. Inspection of the amino acid sequence within the evolutionary conserved C-terminal half of Esp1 revealed that exactly one cysteine and one histidine residue are conserved in all known separin homologues. These two residues might therefore form the catalytic dyad of a new subclass of cysteine protease. When the amino acid sequences surrounding the potential catalytic dyad were further analysed, it was found that both the cysteine and the histidine residues are preceded by a sequence stretch predicted to form a hydrophobic beta sheet. Furthermore, the histidine is invariably flanked by two glycine residues and the cysteine is preceded by a glycine providing the possibility for a tight turns before or after the catalytic residues. This arrangement of histidine and a cysteine catalytic dyad residues fixed at the ends of two neighbouring strands of hydrophobic beta sheet is used in the caspase family of proteases and it seems likely that the same arrangement is used in separins like Esp1.

To provide evidence that Esp1 indeed uses these two amino acid residues histidine (amino acid position 1505) and cysteine (position 1531) as a catalytic dyad for cleaving Scc1, either of these amino acids were mutated to alanine. Both mutations completely abolished the proteolytic activity in yeast extracts after overproduction of the proteins (FIG. 6). Wild type Esp1 overexpressed to a similar level caused complete cleavage of the Scc1 substrate. It was concluded that histidine 1505 and cystein 1531 most likely form the catalytic dyad that provides Esp1 with its proteolytic activity to cleave Scc1.

Together these results provide compelling evidence that a proteolytic reaction in which Esp1 separin cleaves the cohesin Scc1 is the initiating event for sister chromatid separation at the metaphase to anaphase transition in mitosis in *S. cerevisiae*.

It was next asked whether the same proteolytic mechanism might act to initiate chromosome separation during the two meiotic nuclear divisions. During premeiotic DNA replication a Scc1-homolog, called Rec8, replaces Scc1 in the cohesin complex (Klein et al., 1999). Rec8, like Scc1, contains two separin recognition sites, which suggests that Esp1/separin might cleave Rec8 during meiosis to initiate meiotic chromosome separation. To test this, both separin cleavage sites within Rec8 were mutated to produce a non-cleavable version of this protein. Expression of the non-cleavable Rec8 during meiosis led to a block of the first meiotic nuclear division (FIG. 7A), indicating that cleavage of Rec8 is necessary to separate sister chromatid arms in the first meiotic division. When meiosis was followed in a yeast strain containing the esp1-2 mutation, a temperature sensitive mutation in the ESP1 gene, a temperature dependent block of the first meiotic nuclear division was likewise observed (FIG. 7B). It was concluded that separin cleaves the cohesin Rec8 during the meiotic nuclear divisions as it cleaves Scc1 during the mitotic division.

The sequences of human homologs of budding yeast Esp1, Pds1 and Scc1 already exist in public databases. The human homologs of Esp1 and Pds1 are referred to as separin (Nagase et al., 1996; protein sequence: NCBI Acc. No. BM11482; DNA sequence: NCBI Acc. No. D79987) and securin (Zou et al., 1999, Dominguez et al., 1998) respectively, and the human homolog of Scc1 as SCC1 (McKay et al., 1996; DNA sequence: NCBI Acc. No. X98294; protein sequence: NCBI Acc. No. CM 66940). In animal cells it has been shown that the majority of SCC1 dissociates from chromatin in prophase long before sister chromatids are separated in anaphase, and no cleavage of SCC1 has been observed during this process (Losada et al., 1999).

Another object of the experiments of the present invention was to test whether some SCC1 remains bound to condensed chromosomes and maintains sister chromatid cohesion until the initiation of anaphase, and to analyze whether the chromosome-bound form of SCC1 was subject to proteolytic cleavage at the onset of anaphase.

To answer these questions, the following approach was taken: Human HeLa cells were enriched in interphase by logarithmic growth and in metaphase by treatment with nocodazole, and crude chromatin and supernatant fractions were generated by differential centrifugation and analyzed for the presence of SCC1 by quantitative immunoblotting (FIG. 8). The amount of the total cellular SCC1 associated with chromatin was reduced from 56% in logarithmically growing cells to 13% in cells arrested in metaphase. It was concluded that most but not all SCC1 dissociates from chromatin before metaphase, consistent with the possibility that SCC1 may be required to maintain sister chromatid cohesion until the onset of anaphase.

To address whether the form of SCC1 that is associated with chromosomes in metaphase is cleaved in anaphase, HeLa cells were arrested at the onset of S-phase by double-thymidine treatment and were synchronously released into the cell cycle. Progression through the cell cycle was monitored at different time points after the release by analysis of the DNA content with fluorescence activated cell sorting (FACS) and by analyzing total cell lysates in immunoblot experiments. FIG. 9 shows that a putative SCC1 cleavage product corresponding to 100 kDa was recognized by antibodies specific for the C-terminus of SCC1. Importantly, this band appeared specifically when the HeLa cells went through anaphase, as judged by FACS analysis and the disappearance of securin, cyclin B and CDC20, proteins that are known to be degraded specifically in anaphase.

To confirm that the anaphase-specific 100 kDa band is a cleavage product of SCC1 and not a non-specific crossreaction of the antibodies used, the following two experiments were performed: First, antibodies specific for the N-terminus of SCC1 were raised and used to analyze the HeLa cells cycle fractions by immunoblotting. A band of 25 kDa was recognized specifically in anaphase (FIG. 9), consistent with the interpretation that SCC1 is cleaved into an C-terminal 100 kDa and a N-terminal 25 kDa fragment. Second, a HeLa cell line stably expressing mouse SCC1 fused to a myc epitope tag at the C-terminus (SCC1-myc) was analyzed by cell synchronization as above. The amount of SCC1-myc expressed in these cells is less than 10% of endogenous SCC1 and the ectopic protein is entirely incorporated into 14S cohesin complexes (FIG. 10A). In synchronized cells, antibodies to the myc epitope recognize a band of the expected size (120 kDa) that appears in anaphase with similar kinetics as the 100 and 25 kDa bands recognized by SCC1 antibodies, demonstrating unambiguously that mammalian SCC1 is cleaved in anaphase (FIG. 10B). In addition, these immunoblots revealed a second anaphase-specific fragment of SCC1-myc, suggesting that SCC1 cleavage occurs at least two sites (FIG. 10B bottom panel).

Biochemical experiments in *Xenopus* have shown that the initiation of anaphase depends on proteolysis of securin mediated by $APC^{CDC20}$ (Zou et al., 1999). Like budding yeast Pds1 and Esp1, securin and separin form a complex, consistent with the hypothesis that $APC^{CDC20}$-dependent securin proteolysis activates separin. To address whether SCC1 cleavage depends on activation of $APC^{CDC20}$ and subsequent securin proteolysis HeLa cells were synchronized by double-thymidine treatment and released into the cell cycle in the presence of nocodazole. Nocodazole is a drug known to indirectly cause the inhibition of $APC^{CDC20}$ and thereby to arrest cells in metaphase (reviewed by Peters, 1998). Specific antibodies to human securin were raised and it was shown that securin was not degraded under these conditions (FIG. 11). Importantly, no cleavage of SCC1 could be observed in the presence of nocodazole. The effect of the drug was reversible because release of nocodazole arrested cells into anaphase correlated with degradation of securin and formation of the SCC1 cleavage products (FIG. 12). These results suggest that SCC1 cleavage depends on activation of $APC^{CDC20}$ and are consistent with the hypothesis that securin degradation and subsequent separin activation are required for SCC1 cleavage.

To analyze the regulation of SCC1 cleavage further and as a first step to develop a screening assay for inhibitors of this reaction an in vitro assay utilizing SCC1-myc and cell cycle extracts prepared from *Xenopus* eggs was established. These extracts can be manipulated to represent either a stable interphase state in which $APC^{CDC20}$ is inactive or a stable mitotic state in which $APC^{CDC20}$ is active and in which sister chromatid separation can occur in vitro (Murray et al., 1991) When chromatin isolated from HeLa cells stably expressing SCC1-myc was incubated in *Xenopus* extracts, cleavage of SCC1 at two distinct sites could be detected in the mitotic but not in the interphase extract, further confirming that $APC^{CDC20}$ activity is required for this event (FIG. 13). In SDS-PAGE, the cleavage products formed in vitro comigrated with the cleavage products formed in vivo, suggesting that cleavage in the extract occurs at physiologically relevant sites. Importantly, some SCC1 cleavage was also observed when chromatin-free supernatant fractions from HeLa cells were mixed with mitotic extracts (FIG. 13). This demonstrates that soluble human SCC1 can be a substrate for cleavage and thus makes the development of a simplified chromatin-free cleavage assay for drug screening purposes feasible.

To map the more N-terminal cleavage site in SCC1 a series of N- and C-terminal deletion mutants was generated and the electrophoretic mobility of the truncated proteins was compared to the mobility of the N- and C-terminal cleavage products formed in vivo (FIG. 14). cDNAs encoding deletion mutants were generated by polymerase chain reactions (PCR) and recombinant $S^{35}$-labeled proteins were generated from the PCR products by in vitro transcription and translation. This analysis indicated that SCC1 is cleaved between amino acid residues 169 and 183. This site contains the sequence motif $ExxR^{172}$ which is conserved in many SCC1 homologs in different species and is also found in both N-terminal cleavage sites of budding yeast Scc1. Preliminary results using the same mapping strategy indicate that the C-terminal cleavage site in SCC1 is located around amino acid residue 450 where the motif ExxR is found again.

Based on the results of the experiments of the present invention it can be concluded that separin-dependent SCC1 cleavage is a mechanism that is conserved from budding yeast to humans and that the same mechanism most likely exists in all eukaryotic organisms. The findings obtained in experiments performed with budding yeast are therefore also valid in higher eukaryotic organisms, in particular in man.

The interpretation of the data obtained in the experiments of the present invention further provides evidence that Esp1/separin itself is the protease responsible for the cleavage of Scc1p/SCC1.

From the results obtained in the experiments of the invention, it may, inter alia, be concluded that Scc1p/SCC1 is the only subunit of the cohesion comples cleaved by Esp1/separin. This does, however, not exclude the possibility that other types of proteins, for example, other cohesion proteins or proteins which regulate mitotic spindles, might also be targets/substrates of separin. One way of addressing this question is to make a version of Scc1p that has one cleavage site replaced with a site for a foreign protease (with the other cleavage site removed). An example for a convenient protease to use is TEV protease (Daugherty et al., 1989), which has a very specific cleavage site (Glu-Asn-Leu-Tyr-Phe-Gln-Gly (SEQ ID NO:2)). A strain can be constructed that contains: the SCC1 gene containing a TEV protease cleavage site, a chromosomal cdc20-3 mutation, and the TEV protease gene under GAL1-10 inducible control. In the presence of galactose at the restrictive temperature (when cdc20-3 cells are arrested in metaphase due to their failure to destroy Pds1), the effect of the artificial cleavage of Scc1p on its removal from chromosomes can be assayed (as measured by its presence in sedimented chromosomal DNA fractions). Whether or not this is sufficient for sister chromatid separation can also be examined microscopically, using the CenV-GFP system (Ciosk et al., 1998; see Example 3). These experiments allow to determine whether the rest of mitosis can proceed under these conditions in the absence of separin function (note that separin is inactive in cdc20-3 mutants at the restrictive temperature due to the presence of its inhibitor Pds1). If the foreign protease triggers Scc1p's dissociation from chromatids under these circumstances and sister chromatids segregate to opposite poles of the yeast cell, it can be concluded that cleavage of Scc1 is the sole function of separin needed for sister chromatid segregation. If however, sister chromatids fail to segregate to opposite poles of the cell despite the variant Scc1p having been removed from chromatin, then it is concluded that separin has one or more functions besides cleavage of Scc1p. A clue as to these functions can be obtained from the phenotype of these cells and this can be used to identify other potential substrates for Esp1.

The findings of the experiments of the present invention have shed the first key insight into the molecular mechanism by which eukaryotic cells separate sister chromatids. In view of the published literature, which contains no hints as to the mechanism by which sister chromatids are separated, the finding that separins act by conferring a proteolytic activity is highly surprising.

The identification of Esp1/separin as the protease responsible for Scc1/SCC1 cleavage and the identification of potential co-factors, is the prerequisite for designing assay methods that allow for finding compounds interfering with sister chromatid separation, which is the basis for novel therapeutic approaches.

In a first aspect, the invention relates to a method for identifying compounds that have the ability of modulating sister chromatid separation in plant or animal cells, characterized in that a protease with separin-like cysteine endopeptidase activity is incubated, in the presence of the substrate(s) for its proteolytic activity and optionally its co-factor(s), with test compounds and that the modulating effect of the test compounds on the proteolytic activity of the cysteine endopeptidase is determined.

By providing a method to identify compounds which exert their effect by directly modulating, in particular by inhibiting separin's proteolytic activity, i.e. by being protease inhibitors specific for separin, the present invention provides means for interfering with the mechanism of sister chromatid separation and thus a novel approach for inhibiting the proliferation of rapidly dividing animal cells, in particular tumor cells.

In the following, if not otherwise stated, the term "separin" is used as a synonym for any cysteine endopeptidase with separin-like activity, including the yeast homolog Esp1. Similarly, the term "SCC1" is not limited to the human separin substrate, but is intended to encompass any homologous substrate of the cohesin-type.

In a first embodiment, for small scale applications, the assay of the type as described in Example 2 for the yeast components can be used to identify compounds that inhibit separin activity. Given the existence of Esp1 homologues in man, i.e. separin, it can be concluded that the separin activity plays an important role in triggering anaphase onset also in humans. Therefore, a separin-dependent cleavage assay using human separin and SCC1 instead of yeast components can be established using the principles outlined in the experiments for yeast components. Such an assay comprises, as its essential features, incubating a crude preparation of chromatin with a preparation containing a separin activity and determining SCC1 cleavage products in the presence or absence of a test substance.

In general, when setting up a screening assay, it may be useful to first perform it with yeast constituents as assay components and subsequently further develop it stepwise using the protease and/or substrate from intermediate organisms, e.g. from S. pombe or Xenopus laevis, and finally equivalent human substrates. For example, the S. pombe homologue of Scc1 (called Rad21) contains two sequences which are similar to the two known cleavage sites in Scc1, and Rad21 derived sequences may therefore be used to generate a substrate for S. pombe Esp1 (called Cut1). This process of advancing to higher organisms can be applied stepwise until a human system is attained. The cleavage site of any new substrate for human separin can be determined by purifying the cleavage product and determining the N-terminal sequences by Edman degradation as described above.

In a preferred embodiment, the method of the invention is performed on a high-throughput scale. For this embodiment the major assay components, in particular separin, are employed in recombinant form.

Depending on the desired application of the separin-inhibitor to be identified, the assay components employed may vary in terms of the species that they are derived from. In view of therapeutical applications in animals or humans, the assay components are preferably of mammalian or human origin, in case of intended agricultural applications, the assay components are derived from plants.

Separin can be produced recombinantly according to standard methods, e.g in yeast or insect cells or in other suitable host cells, based on the sequence information in the literature or in data bases. The obtained protein can be purified by conventional biochemical fractionation from yeast cells overproducing separin or by tagging the over-produced protein with polypeptide sequences which have a special affinity for a defined ligand (affinity purification). For example, separin can be purified on nickel-agarose columns if it has been tagged with multiple histidine residues, whereas it can be purified on glutathione-agarose columns if it has been tagged with GST. Such affinity purification involves the cleavage of separin from its tag using site specific proteases or self cleaving inteins. The thus obtained recombinant protein can then be used to determine, according to known methods for assaying proteolytic activity, whether separin alone is capable of cleaving Scc1p or peptide substrates derived from it. In case that separin is alone capable of cleaving a SCC1 or a SCC1-derived peptide, an assay based on, preferably recombinant, separin as the protease and its substrate SCC1 can easily be adapted to a high throughput format by methods that are standard for other defined proteases, as described below.

The protease substrates useful in the assay may be those equivalent to or mimicking the naturally occurring substrates, e.g. crude chromatin preparations, SCC1, preferably recombinantly produced, or an SCC1 peptide that contains the proteolytic cleavage site.

Based on information about the sequence specificity of the separin proteolytic cleavage site in yeast and in man, other potential substrates for the protease can be found in other organisms, including humans, which also allows for the design of peptides derived from these substrates, which are useful as substrates in the screening assay of the invention.

In a preferred embodiment, the substrate is a peptide containing the cleavage site of the naturally occurring substrate. The sequence specificity of the proteolytic cleavage can be determined by testing a variety of different peptides. The peptide may be of natural origin, i.e. derived from the natural SCC1, or a variant. An example for a natural peptide is the human SCC1 peptide as set forth SEQ:ID:NO:1, or a fragment thereof that contains the separin cleavage site. Variants can be generated either by synthesising variant peptides or by mutating DNA sequences from genes encoding cohesion proteins. More specifically, other substrates for separin can be identified by searching for small DNA fragments from the yeast genome or an oligonucleotide library that can replace the normal Scc1 cleavage sites. Oligonucleotides may be inserted into a SCC1 gene (lacking both natural cleavage sites) under control of the GAL promoter on centromeric plasmid. Yeast cells may be transformed with a library of such constructs and only plasmids whose modified Scc1 protein can be cleaved by the separin activity will permit growth in the presence of galactose. The peptides encoded by the positive constructs are useful as substrates for separin in the screening assay of the invention.

With regard to the substrate, e.g. the SCC1 protein or a peptide fragment thereof, care needs to be taken that the substrate is efficiently cleaved. It has to be considered, in particular when using the yeast homolog of SCC1, that efficient cleavage appears to occur only when the substrate is in its phosphorylated state, as it is present in mitosis. Therefore, when designing a peptide substrate or when producing SCC1 recombinantly, it has to be tested whether the substrate is efficiently cleaved by separin. In case of the recombinant protein, it can be obtained in its phosphorylated form by producing it in infected insect cells that are treated with a phosphatase inhibitor, e.g. okadaic acid. This method is exemplified, for the yeast Scc1 protein, in Example 5 (method section e) and can, if necessary for other SCC1 molecules, be adapted for these molecules.

In the case that separin does not act by itself, but in cooperation with co-factors, instead of incubating SCC1 (or peptide substrates) with separin alone, they can be incubated with a mixture of separin and its co-factors. All components can be produced and purified according to standard methods as outlined above for separin.

For the high throughput format, the screening methods of the invention to identify separin inhibitors, are carried out according to assay methods known in the art for identifying protease inhibitors. Such assays are based on the detection of the cleavage products of the substrate. To achieve this, an SCC1 peptide or protein substrate that contains cleavage sites for the separin protease is derivatized with a detectable label, e.g. a radioactive or a fluorescent label. Upon cleavage of the substrate by the protease, the cleavage product can be measured. If a test substance is an inhibitor of the protease, there will be, depending on the detection system and depending on whether the test substance has an inhibiting or an activating effect, a decrease or an increase in the detectable signal.

In the high-throughput format, compounds with a modulating effect on separin or a separin-like cysteine endopeptidase can be identified by screening test substances from compound libraries according to known assay principles, e.g. in an automated system on microtiter plates.

Recently, various assay methods for identifying protease inhibitors have been described that are amenable to automation in a high-throughput format, e.g. the radiometric method described by Cerretani et al., 1999, for hepatitis C virus NS3 protease, the method based on fluorescence quenching described by Ambrose et al., 1998, or by Taliani et al., 1996, the microtiter colorimetric assay fot the HIV-1 protease described by Stebbins and Debouck, 1997, the fluorescence polarization assay described by Levine et al., 1997 (reviewed by Jolley, 1996), the method using immobilized peptide substrates described by Singh et al., 1996, the assay used for studying the inhibition of cathepsin G, using biotinylated and cysteine-modified peptides described by Brown et al., 1994. A further example for a suitable assay is based on the phenomenon of fluorescence resonance energy transfer (FRET), as described by Gershkovich et al., 1996 or by Matayoshi et al., 1990. Additional examples for assays that may be used in the present invention for a high-throughput screening method to identify inhibitors of separin activity were described by Gray et al., 1994, Murray et al., 1993, Sarubbi et al., 1991.

Fluorescent or radioactive labels and the other reagents for carrying out the enzymatic reaction on a high-throughput scale are commercially available and can be employed according to supplier's instructions (e.g. Molecular Probes, Wallac). The specific assay design depends on various parameters, e.g. on the size of the substrate used. In the case of using a short peptide, the fluorescence quenching or the fluorescence resonance energy transfer methods are examples for suitable assay technologies.

The fluorescence quenching (Resonance Energy Transfer "RET") assay relies on synthetic substrates which are capable of direct, continuous signal generation that is proportional to the extent of substrate hydrolysis. The substrate peptide carries a fluorescent donor near one end and an acceptor near the other end. The fluorescence of the substrate is initially quenched by intramolecular RET between donor and acceptor. Upon cleavage of the substrate by the protease the cleavage products are released from RET quenching and the a fluorescence proportional to the amount of cleaved substrate can be detected.

An assay of this type may be carried out as follows: the solution of the labeled substrate (e.g. the peptide labeled with 4-[[4'-(dimethylamino)phenyl]azo]benzoic acid (DABCYL) at the one end and with 5-[(2'-aminoethyl)amino]naphtalene-sulfonic acid (EDANS) at the other end or labeled with benzyloxycarbonyl at the one end and with 4-aminomethylcoumarin at the other end) in assay buffer is pipetted into each well of black 96-well microtiter plates. After addition of the test substances in the defined concentration, the separin solution is added to the wells. After incubation under conditions and for a period of time sufficient for the proteolytic cleavage reaction, e.g. for 1 hour at room temperature, the fluorescence is measured in a fluorometer at the excitation wavelength, e.g. at 340 nm, and at the emission wavelength, e.g. at 485 nm.

In the case of using the FRET assay, the following commercially available labeling pairs are suitable for the method of the invention: Europium (Eu) and Allophycocyanin (APC), Eu and Cy5, Eu and PE (Wallac, Turku, Finland).

The compounds identified in the above methods, which are also subject of the invention, have the ability to interfere with sister chromatid separation by modulating the proteolytic activity of a separin-like cysteine endopeptidase.

In a preferred embodiment, the compounds of the invention are inhibitors of a separin-like cysteine endopeptidase.

Preferably, the compounds are specific inhibitors of separin.

The present invention also relates to compounds which act as inhibitors of separin for use in human therapy, in particular cancer therapy.

In a further aspect, the invention relates to a pharmaceutical composition which contains, as the active ingredient, one or more compounds which interfere with or modulate sister chromatid separation by inhibiting the proteolytic activity of separin.

The present invention also encompasses inhibitors of any protease that is recognized to be a separin-like protease because of its sequence similarity to separins; i.e all proteases in which amino acid sequences surrounding the catalytic dyad are more similar to separins than to any class of protease currently known.

In a preferred embodiment, the invention comprises pharmaceutically active compounds and their use in therapy, which are small chemical molecules that have been identified as separin inhibitors in the screening method of the invention.

Alternatively, the separin inhibitors may be biological molecules, e.g. peptides or peptide-derived molecules like peptidomimetics.

Proteases from the caspase family, to which separin is likely to belong, have been shown to be good targets for irreversible binding and inhibition by peptide derived inhibitors (Nicholson et al., 1995; Faleiro et al., 1997). In principle, the approach described for the caspase inhibitors, which act as "recognition site peptides" by being modified to contain an aldehyde, halogenomethyl or acyloxymethyl group at the cleavage position, can be adapted to irreversibly bind to and inhibit the active site cysteine residue in separin. Inhibitory peptide derivatives of this type can be the starting point for rational inhibitor design, e.g. derivatives of the peptide spanning the amino acid sequence at the protease recognition site in SCC1 or another separin substrate. An example for a peptide to be considered for such design is the peptide derived from human SCC1, MDDREIMREGSAFEDDDM (SEQ ID:NO:1), which contains the separin cleavage site, or a mutation or fragment thereof. The inhibitor design can also be aided by obtaining structural information about the catalytic domain of Esp1 using x-ray crystallography. Initially the structure of the Esp1 catalytic domain can also be modelled onto the already known structures of two members of the caspase family of proteases.

The efficacy of compounds identified as separin inhibitors can be tested for in vivo efficacy either on yeast cells or in mammalian cells. Effective compounds should block (or at least in some way interfere with) sister chromatid separation, which can be measured, e.g. by using CenV-GFP in yeast, as described by Ciosk et al., 1998, or standard cytological techniques in mammalian cells. Effective compounds should be either cytostatic or cytotoxic. Substances whose potential for therapeutic use has been confirmed in such secondary screen can be further tested for their effect on tumor cells. To test the inhibition of tumor cell proliferation, primary human tumor cells are incubated with the compound identified in the screen and the inhibition of tumor cell proliferation is tested by conventional methods, e.g. bromo-desoxy-uridine or $^3$H incorporation. Compounds that exhibit an anti-proliferative effect in these assays may be further tested in tumor animal models and used for the therapy of tumors. Toxicity and therapeutic efficacy of the compounds identified as drug candidates by the method of the invention can be determined by standard pharmaceutical procedures, which include conducting cell culture and animal experiments to determine the IC$_{50}$, LD$_{50}$, the ED$_{50}$. The data obtained are used for determining the human dose range, which will also depend on the dosage form (tablets, capsules, aerosol sprays, ampules, etc.) and the administration route (oral, buccal, nasal, paterental or rectal). A pharmaceutical composition containing the compound as the active ingredient can be formulated in conventional manner using one or more physiologically active carriers and excipients. Methods for making such formulations can be found in manuals, e.g. "Remington Pharmaceutical Sciences".

Influencing the process of sister chromatid separation may be also beneficial in preventing birth defects caused by missegregation of chromosomes in human meioses. For example, since cases of human aneuploidy such as Down's syndrome may be caused by premature separation of sister chromatids (Griffin, 1996), the use of a drug that inhibits separin activity might be able to reduce precocious sister separation and thereby the incidence of aneuploidy in human fetuses. Thus, in a further aspect, the invention relates to separin inhibitors for the prevention of birth defects caused by missegration of chromosomes in human meioses.

Separin inhibitors may also be useful in applications which aim at the deliberate polyploidisation of plant cells for crop development. In yeast, it has been shown that inhibition of separin activity prevents chromosome separation without blocking cell cycle progression and therefore gives rise to cells with increased ploidy. Inhibitors that block separin's protease activity could therefore be used to increase the ploidy of any eukaryotic cell, including all plant cells. Increasing the ploidy of plant cells is useful for 1) producing larger plants, 2) for increasing the ploidy of breeding stocks, and 3) for generating fertile hybrids.

Therefore, the present invention relates, in a further aspect, to separin inhibitors for the treatment of plant cells for increasing their ploidy.

To identify separin inhibitors that are useful for the above-mentioned agricultural purposes, the screening method of the invention can be easily adapted by employing plant components, i.e. a plant separin and a plant homolog of SCC1. Sequence homologs of plant separin and SCC1 are present in databases, e.g. of the *Arabidopsis thaliana* genome.

Separin inhibitors which impair sister chromatid separation may also be used in cytological analyses of chromosomes, for example, in medical diagnoses of chromosome structure.

BRIEF DESCRIPTION OF THE FIGURES

FIG. 3: Detection of the Scc1p cleavage product in vivo in cells passing synchronously through the metaphase to anaphase transition FIG. 7: Separin cleavage of the cohesin Rec8 is necessary during meiotic nuclear divisions FIG. 14: Mapping of the N-terminal cleavage site of human SCC1

Figure 1:
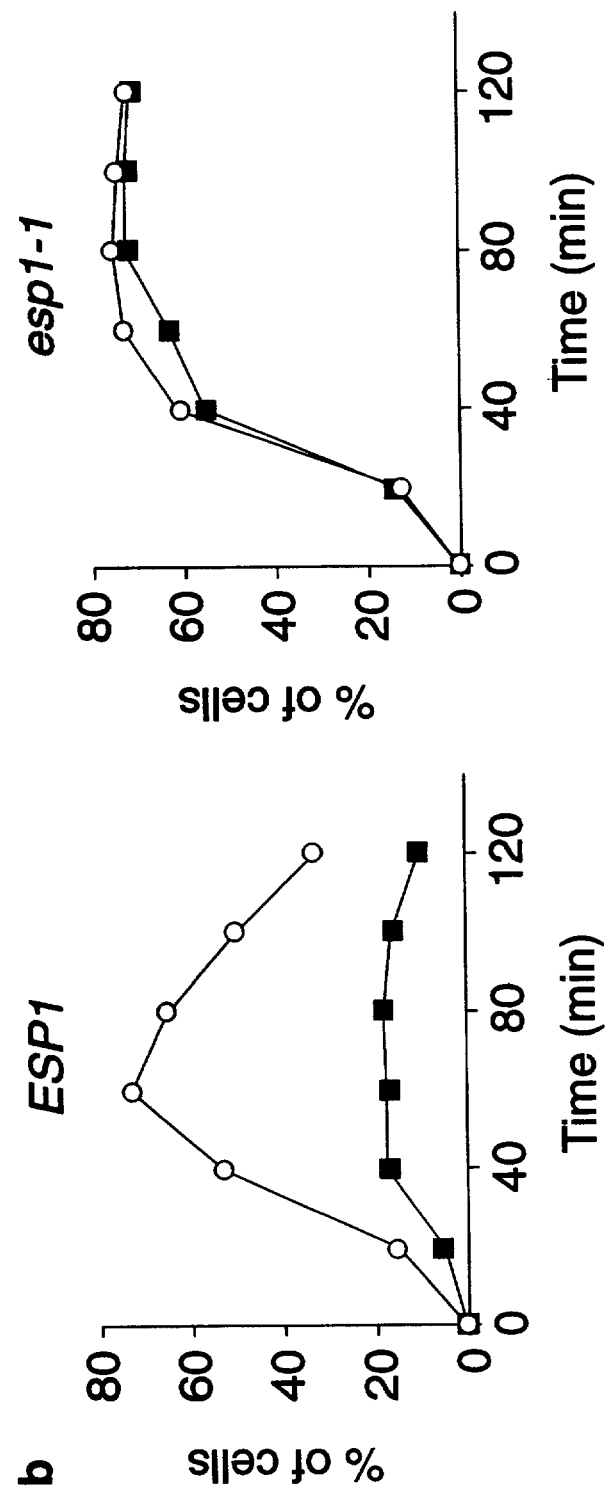
FIG. 1: Chromosome association of Scc1p in G1 is Esp1-dependent

If not otherwise stated, the following materials and methods were used in the experiments of the present invention a) Yeast Plasmids and Strains:

The Scc1p coding sequence (Saccharomyces Genome Database YDL003W) was cloned under control of the GAL1-10 promoter in a Ylplac128 derived vector (Gietz and Sugino, 1988), and under its own promoter into YCplac111 (Gietz and Sugino, 1988) using the polymerase chain reaction (PCR). DNA fragments encoding multiple HA and myc epitopes were inserted into restriction sites introduced by PCR at the N- and C-termini of SCC1. Site directed mutagenesis was performed by PCR using primers containing the desired nucleotide changes. The validity of all constructs was verified by nucleotide sequencing.

All strains used were derivatives of W303 (HMLa HMRa ho ade2-1 trp1-1 can1-100 leu2-3,112 his3-11, 15 ura3). Epitope tags at the endogenous Scc1p were generated by a PCR one-step tagging method (Michaelis et al., 1997). A strain overexpressing Esp1p from the GAL1-10 promoter was described (Ciosk et al., 1998) and crossed to a strain containing the esp1-1 mutation (McGrew et al., 1992). A strain expressing the sole source of Cdc20p under control of the GAL1-10 promoter was described in (Lim et al., 1998). To visualize sister chromatids a Tet repressor-GFP fusion protein is synthesized in the cells that binds to a cluster of Tet operator sequences integrated at the URA3 locus close to the centromere of chromosome V as described in (Michaelis et al., 1997).

All meiotic yeast strains used in Example 7 are derivatives of the rapidly sporulating SK1. The Rec8 431/453 mutant (E428R R431E R453E) was generated by site-specific mutagenic PCR of a REC8 wild-type integrative plasmid. This YIplac128-derived plasmid (Gietz and Sugino, 1988) contains the REC8 gene and promoter and 3 HA epitope sequences at the C-terminus. This plasmid was integrated at the rec8::KanMX4 locus by transformation with the MluI-linearized plasmid.

The esp1-2 allele (McGrew et al., 1992) was recovered from strain K8493 using a gap repair strategy as described by Guthrie and Fink, 1991. The recovered allele was transferred into SK1 by transformation and 5-FOA counter-selection (Guthrie and Fink, 1991). The resultant temperature-sensitive strain was diploidized by transformation with plasmid c1743 containing the HO gene. For sporulation experiments, strains were first streaked from the –80° C. stock onto a YEPGlycerol plate and grown for 60 hours at 25° C. A single colony was patched onto YEPD and grown for 48 hours at 25° C. The patch of cells was innoculated into liquid YEPD and grown for 8 hours to stationary phase. The culture was washed with YEPA and grown overnight in YEPA. Cells were washed with 2% Potassium Acetate and then incubated for 14-24 hours in the same medium. Samples were taken every two hours and fixed with 70% ethanol for visualizing nuclei by DAPI staining.

b) Yeast Cell Growth and Cell Cycle Experiments

Cells were grown in complete medium (Rose et al., 1990) at 25° C. if not otherwise stated. Strains expressing Cdc20p, Esp1p, or Scc1p from the GAL1-10 promoter were grown in complete medium containing 2% Raffinose as carbon source. The GAL1-10 promoter was induced by adding 2% galactose. A G1 like arrest was achieved by adding 1 µg/ml of the pheromone alpha factor to the medium. For a metaphase arrest, 15 µg/ml nocodazole was added with 1% DMSO. Metaphase arrest due to Cdc20p depletion was obtained in cells with the sole source of Cdc20p under control of the GAL1-10 promoter. A logarithmically growing culture in complete medium containing raffinose and galactose was filtered, washed with medium containing Raffinose only, and resuspended in the same medium. For release from the arrest 2% Galactose was added back to the culture.

c) In Vitro Assay for Yeast Esp1p Activity

A crude Triton X-100 insoluble chromatin preparation was obtained from yeast cells as described (Liang and Stillman, 1997). The pelleted chromatin was resuspended in yeast cell extracts that had been prepared similar to the supernatant fraction of the chromatin preparation. One tenth volume of an ATP regenerating system was added (50 mM HEPES/KOH pH-7.5, 100 mM KCl, 10 mM $MgCl_2$, 10 mM ATP, 600 mM creatin phosphate, 1.5 mg/ml phophocreatin kinase, 1 mM DTT, 10% glycerol). Reactions were incubated for 10 min at 25° C. with shaking and stopped on ice. The chromatin fraction was separated again from the supernatant by centrifugation, and resuspended in buffer EBX (Liang and Stillman, 1997). Equivalent aliquots of supernatant and chromatin pellet were analysed by SDS-PAGE and Western blotting. Scc1-HA was detected with the anti-HA monoclonal antibody 16B12 (Boehringer Mannheim).

Since overexpression of Esp1p from the GAL1-10 promoter is toxic to cells, extracts with overproduced Esp1p were prepared 2 h after induction with galactose of a culture pregrown in medium containing raffinose only.

d) Protein Sequencing of the Yeast Scc1p Cleavage Site

The C-terminal Scc1p cleavage fragment was isolated from cells that contained Scc1p tagged with 18 tandem myc epitopes at the C-terminus. A Cdc20 arrest/release strategy was employed to obtain cells containing a high portion of Scc1p in the cleaved form. Protein extract of $5 \times 10^9$ cells was prepared by breakage with glass beads 15 min after release from the metaphase arrest. Myc-epitope tagged protein was immunoprecipitated with 20 mg anti-myc 9E11 monoclonal antibody under denaturing conditions and resolved on SDS-PAGE next to size markers. Proteins were transferred to a PVDF membrane and stained with Coomassie Brilliant Blue R250. N-terminal sequencing of the band corresponding to the Scc1p cleavage fragment yielded the amino acid sequence RLGESIM (SEQ ID NO: 4) (Scc1p amino acids 269 onwards).

e) Purification of Yeast Scc1 Expressed in Baculovirus Infected Insect Cells

The Scc1 coding sequence was cloned into the baculovirus transfer vector pFastBac1 (Gibco Life Technologies). At the C-terminus a FLAG epitope tag was added followed by a cassette containing the yeast VMA intein and a chitin binding domain (New England Biolabs). Recombinant baculoviruses were obtained following the manufacturer's instructions. HiFive insect cells (Invitrogen) were grown in monolayers to confluency and infected at an multiplicity of infection of 2 with the recombinant baculovirus. To obtain metaphase-like phosphorylation 0.1 M Okadaic acid was added 40 hours after infection. 43 hours after infection cells were harvested. Cytoplasmic and nuclear extracts were obtained as described (Cai et al., 1996). Scc1 was purified from the combined extracts by chitin affinity chromatography according to the manufacturer's protocols, and further purified by two subsequent ion exchange chromatography steps on a MonoQ column (Amersham Pharmacia).

f) Mutations in the Yeast Esp1 Catalytic Dyad

Esp1 was overexpressed as described in a). The conserved residues histidine 1505 and cysteine 1531 that form the putative catalytic dyad of the Esp1 protease were changed to alanine using a PCR based mutation scheme. The mutant proteins were expressed from the GAL promoter in yeast and assayed for there cleavage activity as described under c).

g) Other Yeast Methods

Analysis of DNA content was performed as described (Epstein and Cross, 1992) on a Becton Dickinson FACScan, chromosome spreads were as described (Michaelis et al., 1997), photo micrographs were taken with a Photometrics CCD camera mounted on a Zeiss Axiophot microscope.

In vitro translation of Pds1p was performed in reticulocyte lysate using the TNT system (Promega).

h) Human Cells

HeLa cells were cultivated in DMEM supplemented with 10% FCS at 37° C. and 5% $CO_2$.

In some experiments HeLa cells stably expressing mouse SCC1 fused to 9 myc ecpitopes at its C-terminus were used.

i) Human Cell Cycle Experiments

For cell cycle synchronization, a double-thymidine treatment was used. HeLa cells were first treated with 2 mM thymidine for 18 h. Subsequently, cells were washed with PBS, fresh medium was added and the cells were grown for another 8 h. Then the cells were treated again with 2 mM thymidine for 18 h, subsequently washed and incubated in fresh medium. Samples were taken at different time points. Samples were splitted and used for FACscan analysis and for immunoblotting. Cell extracts were made with glass-teflon potters in ice cold buffer containing 50 mM Tris pH 7.7, 100 mM NaCl, 20 mM b-glycerophosphate, 5 mM $MgCl_2$, 1 mM NaF, 0.1-0.2% Triton X-100, 10% Glycerol, 1 mM DTT and protease inhibitors).

In some experiments logarithmically growing HeLa cells were treated with 330 nM nocodazole dissolved in 0.1% DMSO for 18 hours, or cells synchronized by double-thymidine treatment were released into nocodazole-containing medium for different periods of time. In control experiments 0.1% DMSO was added without nocodazole.

For SDS-PAGE, equal amounts of total extract was loaded (usually 50 g protein per sample). For western blotting the following antibodies were used: Monoclonal mouse-anti-separin a C-terminal fragment of human separin was expressed in pET28Vector, His-tagged protein was purified and used for immunization); rabbit-anti-SCC1 (N-terminal or C-terminal peptides of human SCC1 were coupled to KLH and used for immunization); rabbit anti-securin (human securin was expressed in pTrcHis2 vector, His/myc-tagged protein was purified and used for immunization). All antibodies were affinity purified. CDC27, CDC20 and proteasome antibodies have been described (Gieffers et al., 1999). Mouse-anti-Cyclin B1 (#SC-245) were from Santa Cruz Biotechnology, USA. Rabbit-anti-Cyclin A (#06-138) and rabbit-anti-pho-pho-Histone H3 (#06-570) were from Upstate Biotechnology, USA. Rabbit-anti-myc-epitope antibodies (CM-100) were from Gramsch, Germany.

j) In Vitro Cleavage of SCC1-myc

Whole cell extract (containing 250 μg protein) from nocodazole-arrested HeLa cells ectopically expressing mouse SCC1-myc was separated by centrifugation into chromatin and supernatant fractions. Either 12.5 ul of the supernatant fraction or the chromatin pellet (resuspended in 5 ul of buffer containing 0.005% Triton X100, 20 mM Hepes pH 7.7, 20 mM KCl, 1 mM $MgCl_2$, 2 mM $CaCl_2$) were incubated with 25 μl of either interphase or mitotic *Xenopus* egg extract at room temperature. At different time points samples were taken, separated by SDS-PAGE and analyzed by immunoblotting with anti-myc antibodies. *Xenopus* extracts were prepared as described (Murray, 1991).

k) Mapping of the N-Terminal Cleavage Site of Human SCC1

For generating truncated versions of the human SCC1 cDNA, polymerase chain reactions (PCRs) were used. For N-terminal deletions different 5'-primers containing T7 promotor regions, a start codon and appropriate SCC1 sequences were used. For C-terminal deletions different 3'-primers with appropriate SCC1 sequences and a stop-codon were used. The obtained PCR fragments were transcribed and translated in the presence of $^{35}$S-methionine in reticulocyte lysate in vitro (TNT system, Promega). The in vitro translated products were separated by SDS-PAGE and immunoblotted with C- or N-terminal specific SCC1 antibodies.

EXAMPLE 1

Chromosome Association of Yeast Scc1p in G1 is Esp1-Dependent

A) Cells, wild type for ESP1 or containing the esp1-1 mutation, with an unmodified endogenous copy of Scc1 and a second myc-tagged copy under the control of the GAL promoter were arrested with the mating pheromone alpha factor for 120 min. All cells had then arrested in the G1 phase of the cell cycle (time point 0 of the experiment). The FACScan profile of the DNA content is shown, demonstrating that all cells stayed arrested during the following 120 min time course of the experiment. Scc1 myc was induced for 60 min by adding 2% galactose, then cells were transferred to medium containing 2% glucose to repress Scc1 myc expression (FIG. 1A).

B) Expression of Scc1 myc was seen by whole cell in situ hybridization (open circles), and chromosome binding of Scc1 myc was observed using chromosome spreads (filled squares). The percentage of cells positive for Scc1 myc expression and that had Scc1 myc bound to chromosomes is shown in the graphs (FIG. 1B).

EXAMPLE 2

In Vitro Assay for Yeast Scc1p Cleavage and Dissociation from Chromatin

Figure 2:
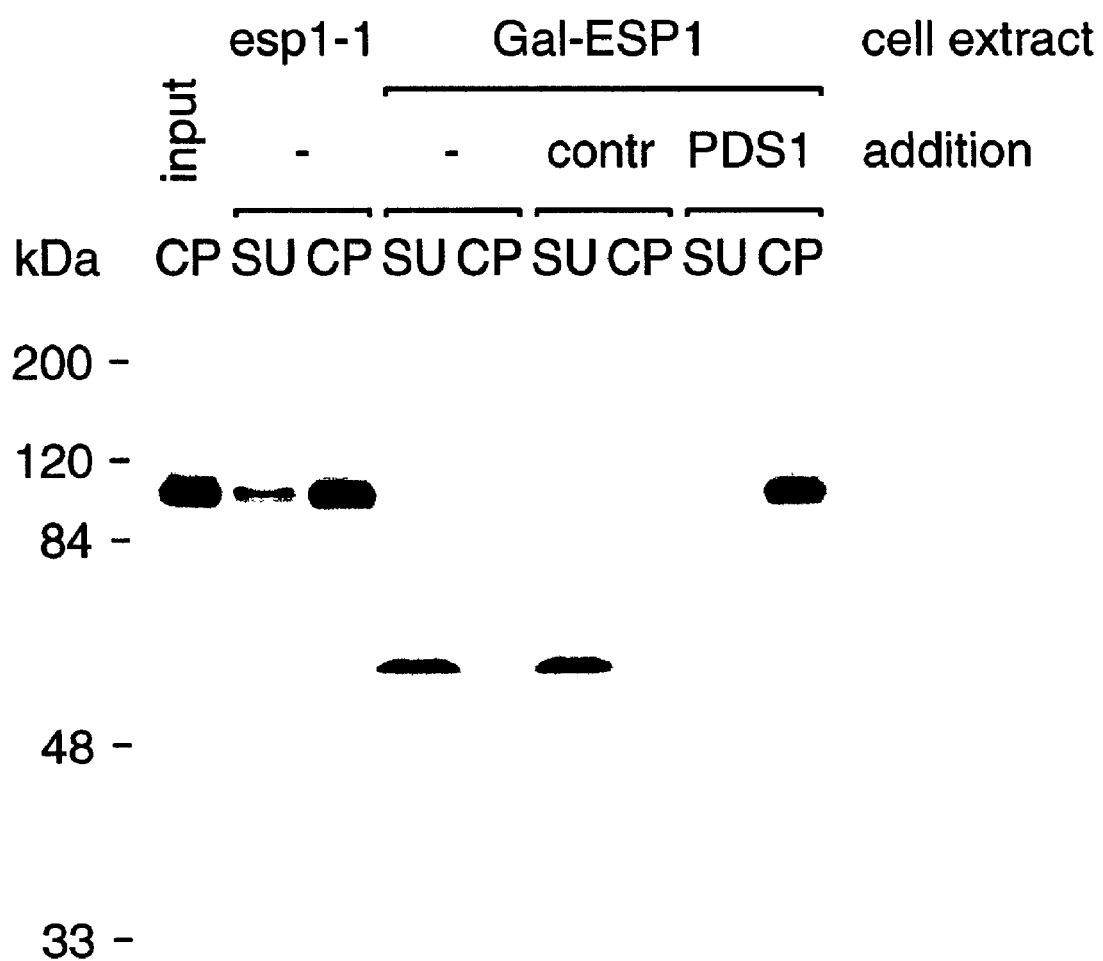
FIG. 2: In vitro assay for Scc1p cleavage and dissociation from chromatin

Chromatin was prepared from a strain containing Scc1p tagged with HA epitopes that was arrested in metaphase with nocodazol. The proteins in the chromatin preparation were resolved by SDS-PAGE and Scc1-HA was detected by western blotting (FIG. 2, lane 1). This chromatin preparation was resuspended in the indicated extracts, with or without addition of in vitro translation products as indicated. Incubation was for 10 min at 25° C., after which the chromatin was separated again from the supernatant by centrifugation. Aliquots of the supernatant fraction and the chromatin fraction of each reaction were analysed.

EXAMPLE 3

Detection of the Yeast Scc1p Cleavage Product in Vivo in Cells Passing Synchronously through the Metaphase to Anaphase Transition The strain used expressed Cdc20p under the control of the GAL promoter as the only source of Cdc20p. Scc1p was tagged with HA epitopes, and sister chromatids were visualized by tetR-GFP bound to tetO sequences inserted at the centromere of chromosome V. Cells were arrested at metaphase by depleting the cells of Cdc20p in medium lacking galactose for 120 min. Then 2% galactose was added to induce Cdc20p synthesis.

A) The FACscan profile of the time course is shown in FIG. 3A.

B) Budding (FIG. 3b, filled squares) was scored, all cells arrested after 120 min with large buds and cytokinesis happened for most cells between 30 min and 45 min after induction of Cdc20p synthesis. Scc1-HA bound to chromosomes was seen on chromosome spreads (FIG. 3B, open circles) in most cells in the arrest, and Scc1-HA disappeared from chromosomes within 15 min after release. The percentage of cells with separated sister chromatids as seen as the occurrence of two separated GFP dots in one cell body is presented (FIG. 3B, filled triangles).

C) Examples of cells in the arrest at 120 min and 15 min after release. The synchronous separation of sister chromatids is visible as separating GFP dots (FIG. 3C).

D) Western blot analysis of whole cell extracts at the indicated time points. The cleavage fragment of Scc1-HA is apparent at 135 min short after the release from the metaphase block into anaphase (FIG. 3D).

EXAMPLE 4

Figure 4:
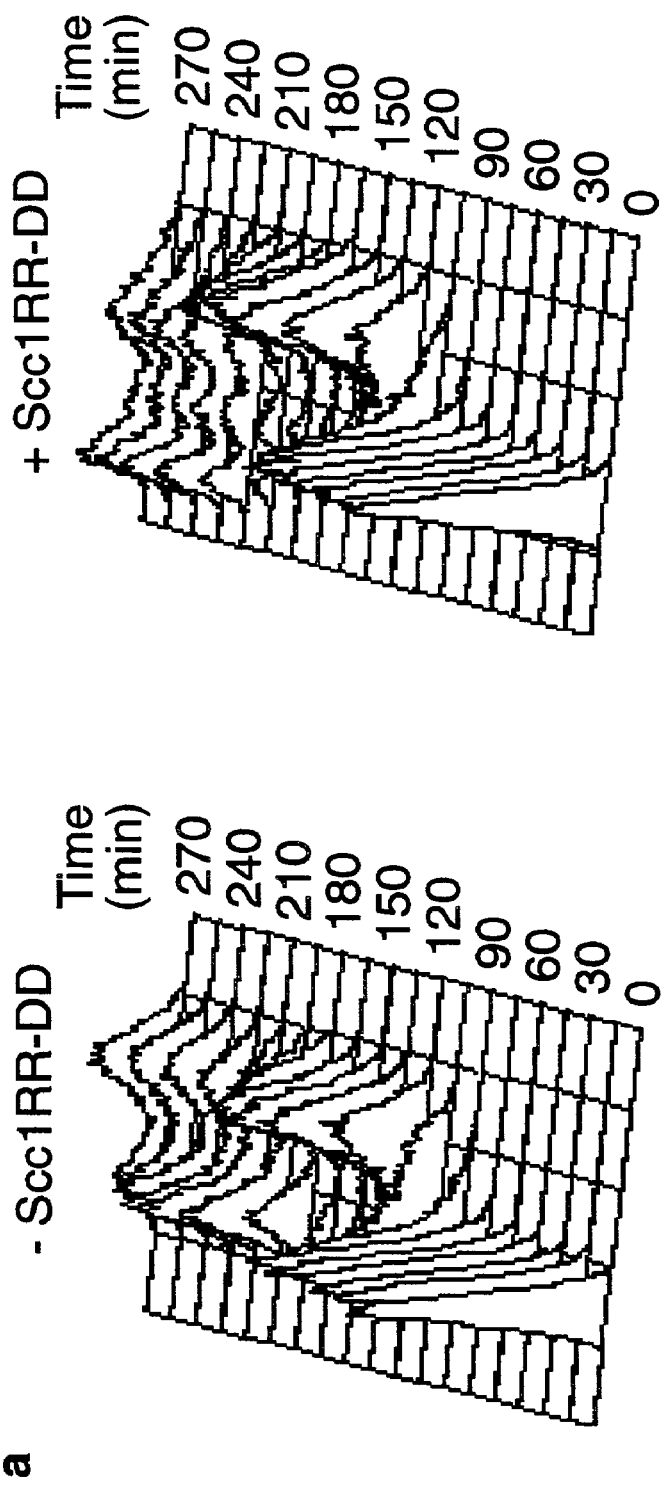
FIG. 4: Expression of a non-cleavable variant of Scc1p prevents Scc1p dissociation from chromosomes and sister chromatid separation in vivo
Figure 4:
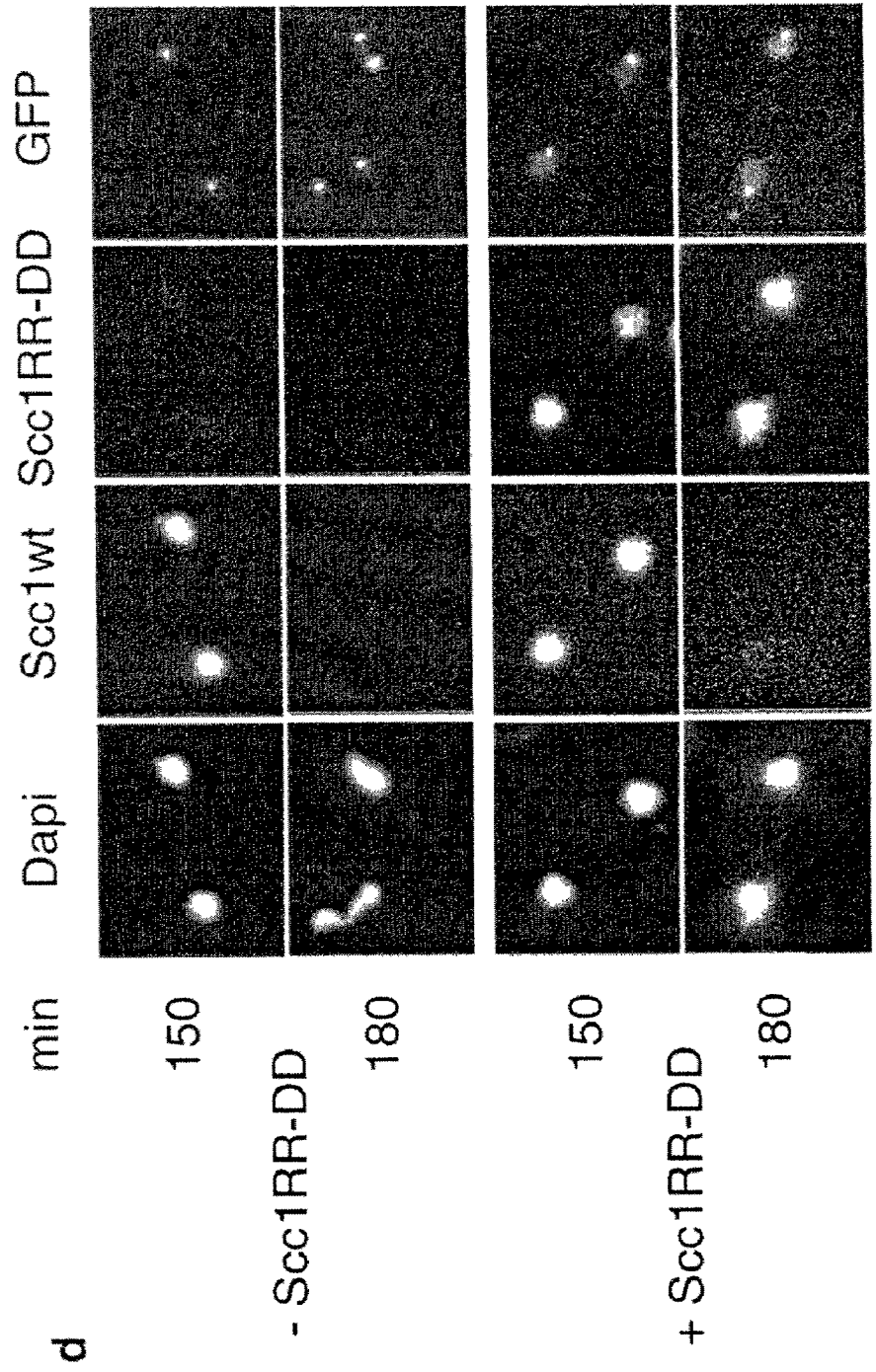

Expression of a Non-Cleavable Variant of Yeast Scc1p Prevents Scc1p Dissociation from Chromosomes and Sister Chromatid Separation In Vivo A) FACscan profile of the DNA content as unbudded G1 cells were released into the cell cycle either with or without the induction of the Scc1RR-DD mutant (FIG. 4A).

B) Budding index without (FIG. 4B, open squares) or with (FIG. 4B, open triangles) induction of Scc1RR-DD. Sister chromatid separation in the cells was monitored by counting the percentage of cells containing two separated GFP dots (FIG. 4B, filled squares for the control culture not expressing Scc1RR-DD, and filled triangles for the culture expressing Scc1RR-DD).

C) Scc1p chromosome association was measured on chromosome spreads. The endogenous wild type Scc1 myc is shown for the control cells (open squares) and cells expressing Scc1RR-DD (FIG. 4c, open triangles). The Scc1RR-DD was HA tagged and detected on chromosome spreads of the induced culture (FIG. 4C, filled triangles).

D) Examples of chromosome spreads of both cultures at 150 min in metaphase and at 180 min when most cells of the control culture had undergone anaphase. The DNA was stained with DAPI, Scc1 myc was detected with a rabbit-anti-myc antiserum and anti-rabbit-Cy5 conjugated secondary antibody, Scc1RR-DD-HA was detected with the mouse monoclonal antibody 16B12 and anti-mouse-Cy3 conjugated secondary antibody. Sister chromatids of centromere V were visualized by the GFP dots (FIG. 4D).

EXAMPLE 5

Purified Yeast Scc1 is a Substrate for Esp1-Dependent Cleavage

Figure 5:
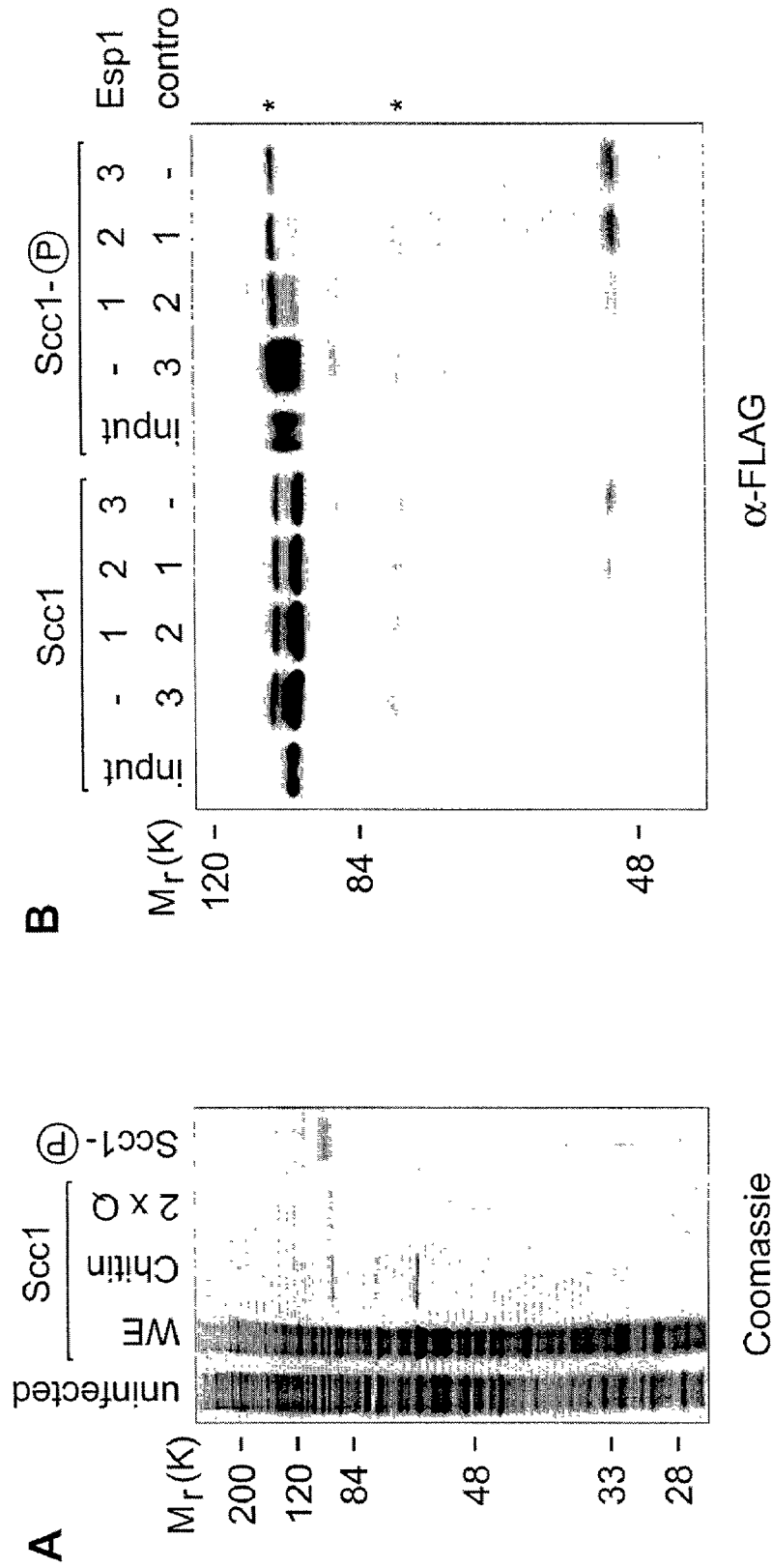
FIG. 5: Purified Scc1 is a substrate for the Esp1-dependent cleavage reaction

FIG. 5A: Purification of Scc1 from baculovirus-infected insect cells. SDS-PAGE followed by staining with Coomassie brilliant blue R250 of control HiFive whole cell extract (lane 1), whole cell extract after infection with the virus expressing Scc1 (lane 2), the eluate from the chitin affinity column (lane 3), and the pooled fraction of the second MonoQ chromatographic step (lane 4). Scc1, purified in a similar way, but containing metaphase-like phosphorylation, is shown in lane 5.

FIG. 5B: Cleavage assay using purified Scc1. Purified Scc1 in both the unphosphorylated and the metaphase-like phosphorylated form was used as a substrate in a cleavage assay. The cell extract containing Esp1 was as in FIG. 2, but was used mixed in different ratios with the control extract to obtain a titration of the Esp1 activity. Scc1 was detected by Western blotting with the anti-FLAG monoclonal antibody M2 (Sigma).

EXAMPLE 6

Figure 6:
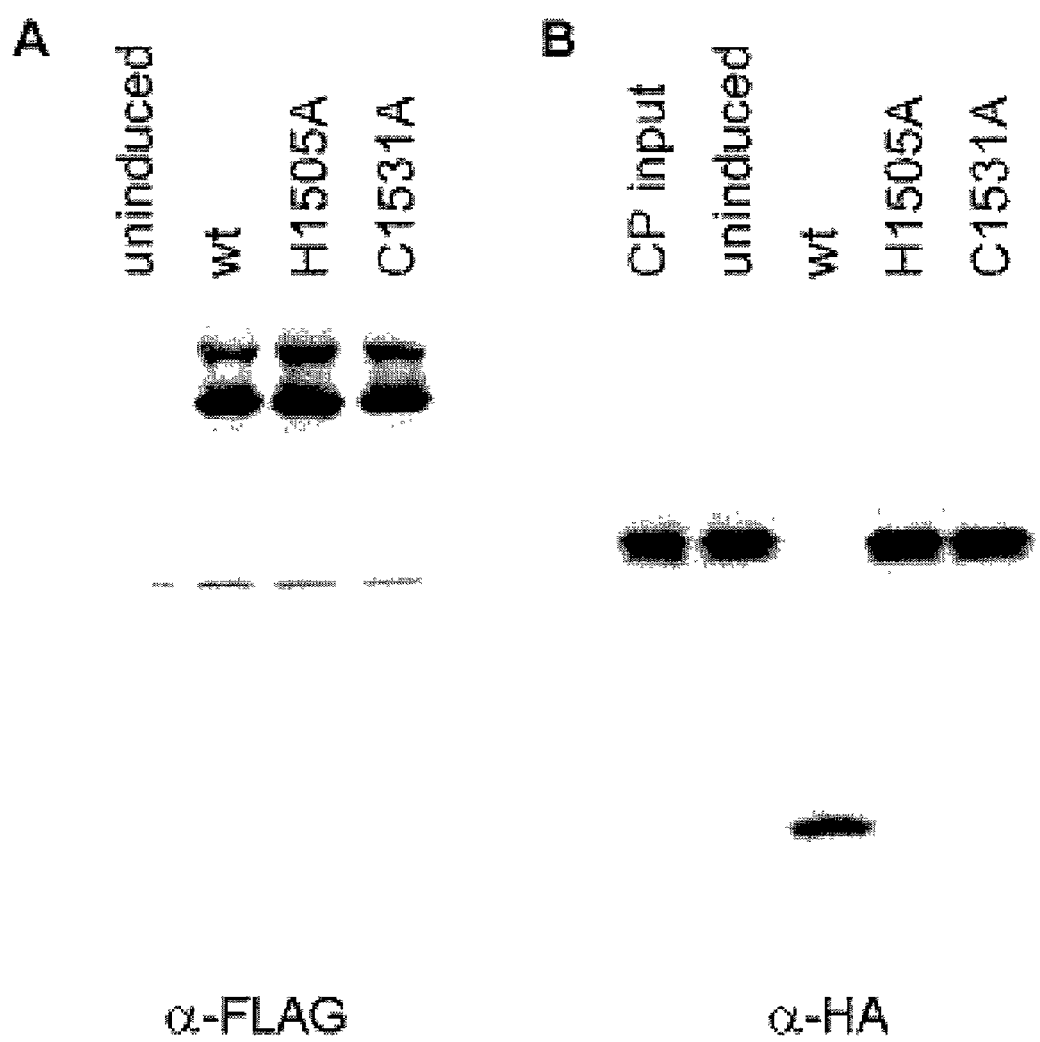
FIG. 6: Mutations in the putative catalytic dyad of the Esp1 protease domain abolish cleavage activity

Mutation of the catalytic dyad in yeast Esp1 abolishes its cleavage activity. Wildtype Esp1 and mutants H1505A and C1531A were overexpressed in yeast, tagged with a FLAG epitope for detection. FIG. 6A: Western blot of cell extracts showing that the two mutant Esp1 proteins were expressed as stable proteins to similar levels as the wild type protein. FIG. 6B: The associated Scc1 cleavage activity was assayed as in Example 2.

EXAMPLE 7

Preventing Cleavage of the Meiotic Cohesion Protein Rec8 by Mutations in its Cleavage Sites or by an esp1 Mutation Inhibits Meiotic Nuclear Divisions FIG. 7A: Diploid yeast strains either wild type for Rec8 or expressing Rec8 with both cleavage sites mutated were sporulated. The percentage of cells containing either one nucleus, two nuclei, or three or four nuclei is depicted throughout the time course of the experiment.

FIG. 7B: A diploid yeast strain homozygous for the esp1-2 mutation was sporulated at 25° C. or 35° C. The percentage of cells containing either one nucleus, two nuclei, or three or four nuclei is depicted.

EXAMPLE 8

Association of Human SCC1 with Chromatin

Figure 8:
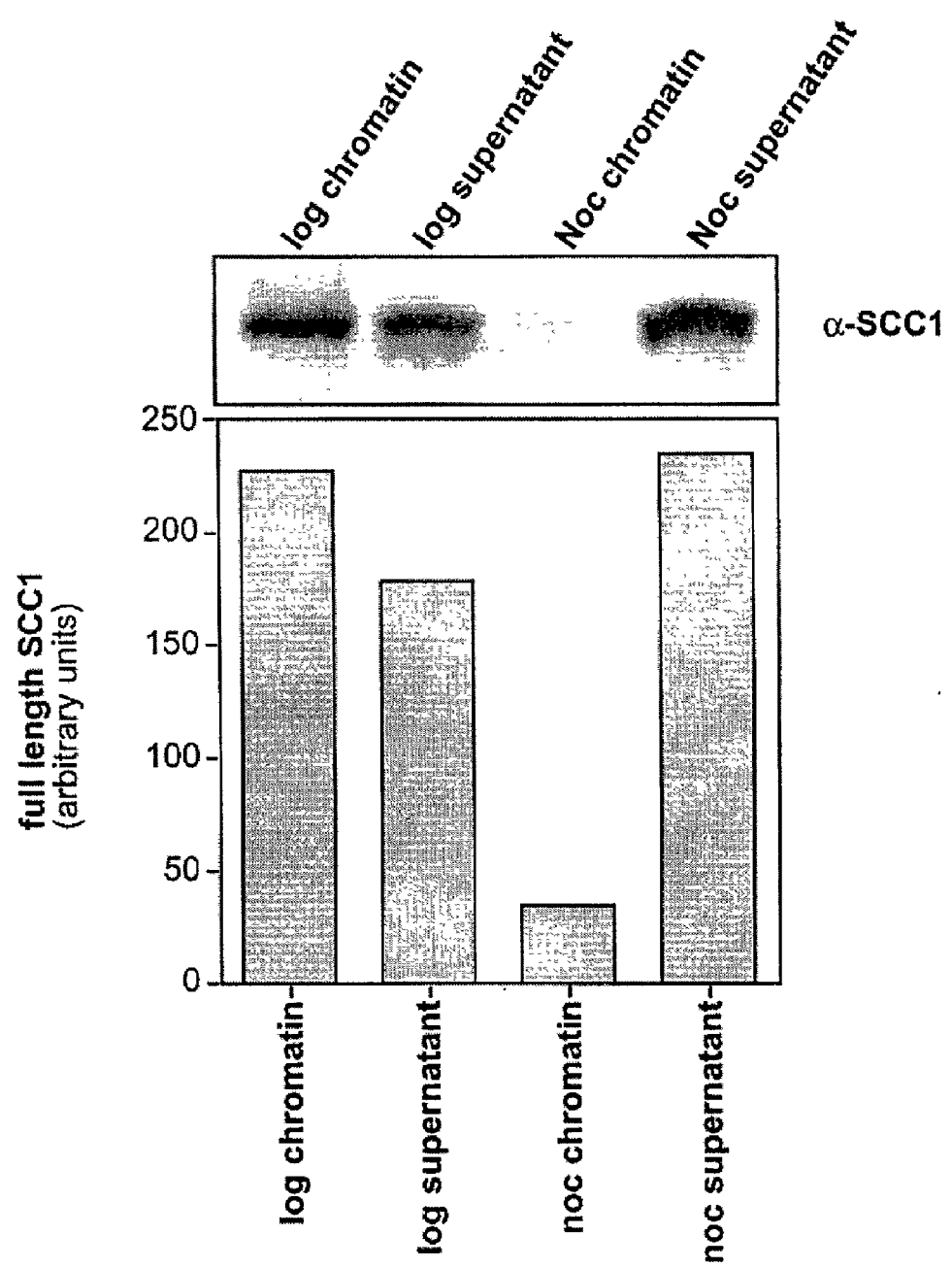
FIG. 8: Association of human SCC1 with chromatin

Chromatin and supernatant fractions were prepared from HeLa cells that were either growing logarithmically (log) or were arrested in metaphase with nocodazole (noc). Proteins from equivalent aliquots of these fractions were separated by SDS-PAGE and analyzed for the presence of SCC1 by immunoblotting using radiolabeled antibodies (FIG. 8, top panel), The intensities of the SCC1 bands were quantitated (FIG. 8, bottom panel).

EXAMPLE 9

Human SCC1 is Cleaved in Mitosis

Figure 9:
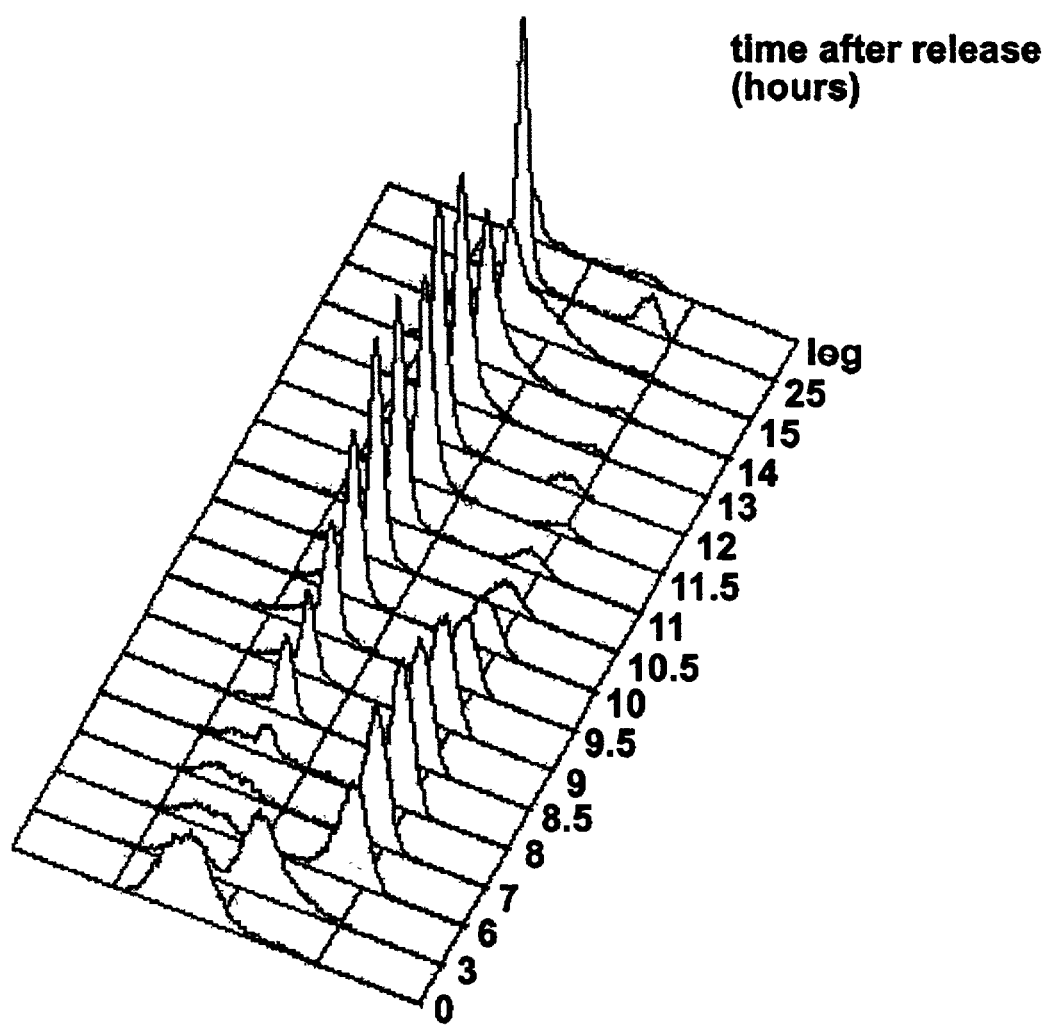
FIG. 9: Human SCC1 is cleaved in mitosis
Figure 9B:
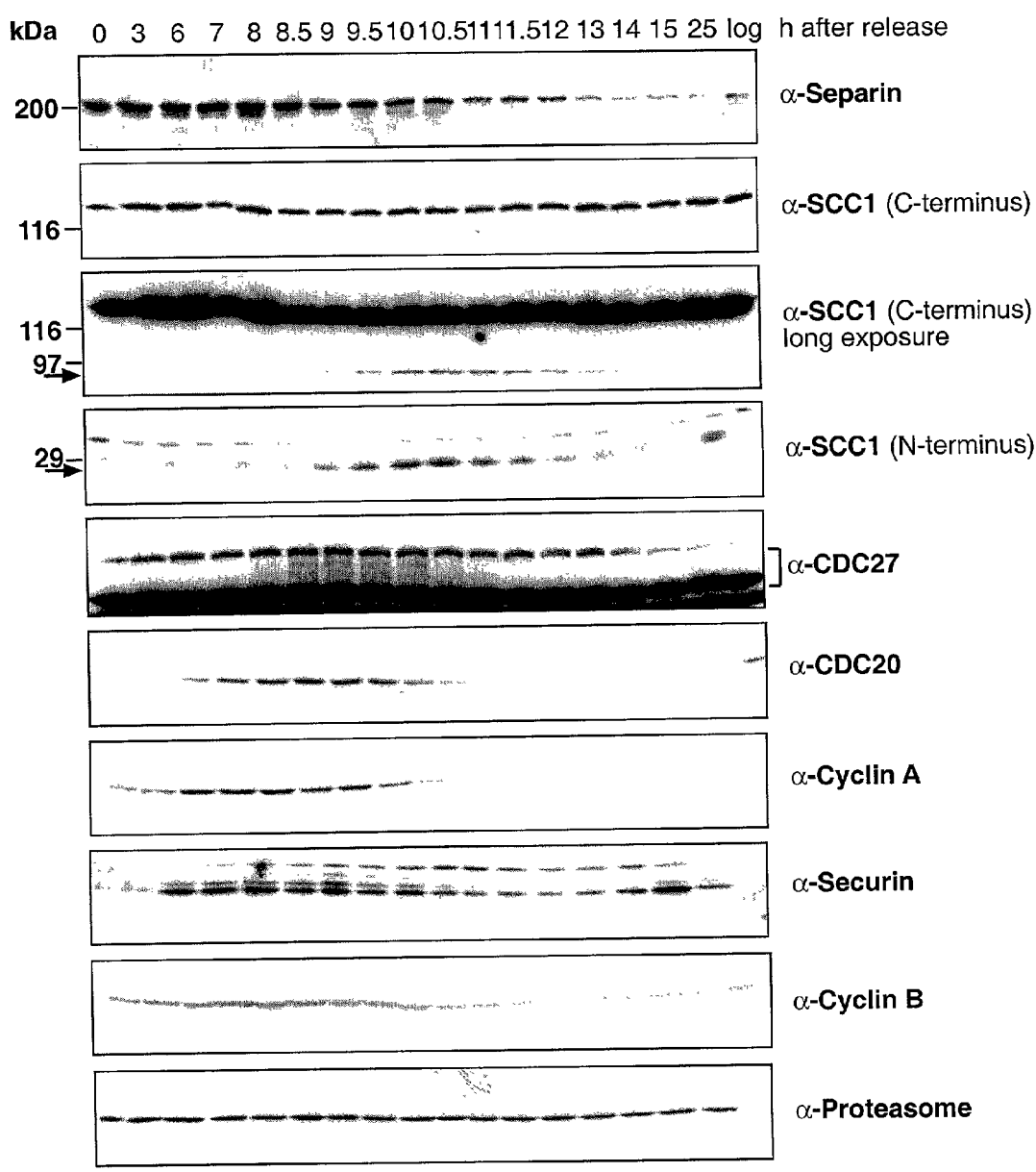

HeLa cells were arrested at the onset of S-Phase by a double-thymidine treatment and were synchronously released into the cell cycle. Samples were taken at the indicated time points. Cells were analyzed for their DNA content by FACscan (FIG. 9A) and by SDS-PAGE and immunoblotting of whole cell extracts using the indicated antibodies (FIG. 9B). The phosphorylation-dependent electrophoretic mobility shift of the APC subunit CDC27 was used as a marker for mitotic entry. The disappearance of cyclin A was used as a marker for metaphase, and the disappearance of CDC20, securin and cyclin B as a marker for anaphase. Proteasome levels were determined as a loading control. The arrows in panels 3 and 4 of FIG. 9B from the top indicate 100 and 25 kDa bands that are recognized by antibodies that are specific for the C- and the N-terminus of SCC1, respectively.

EXAMPLE 10

Figure 10:
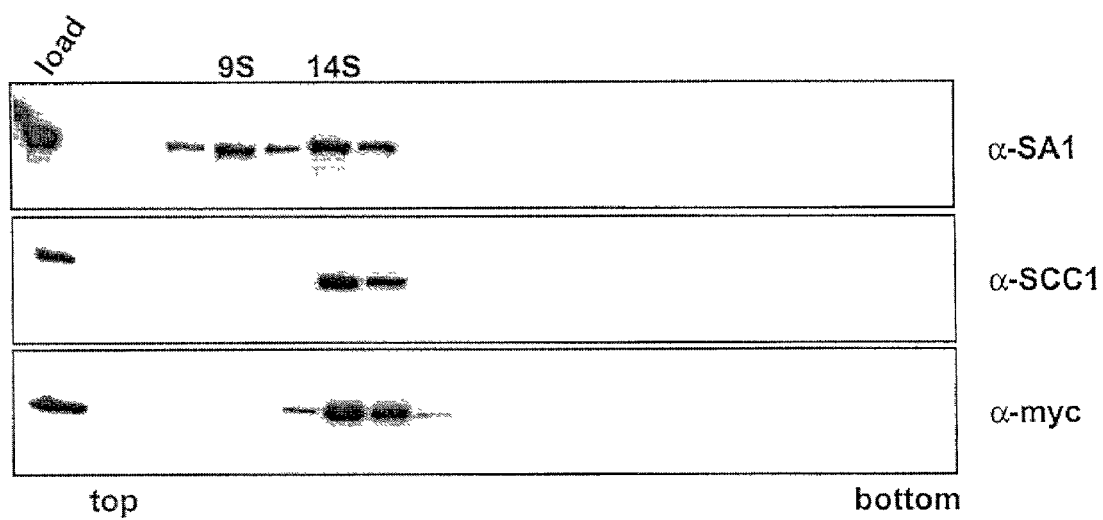
FIG. 10: Ectopically expressed SCC1-myc is incorporated into the cohesin complex and is cleaved in mitosis
Figure 10:
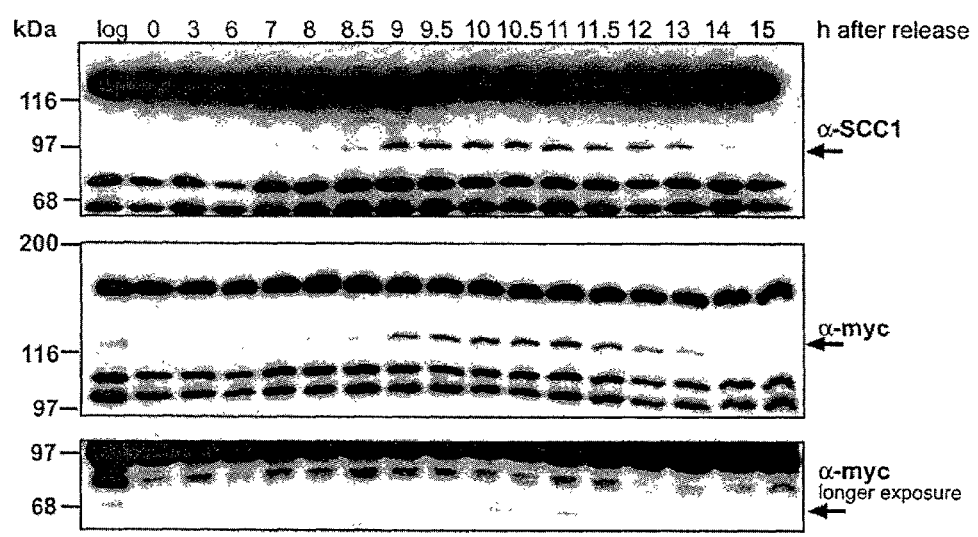

Ectopically Expressed SCC1-myc is Incorporated into the Cohesin Complex and is Cleaved in Mitosis FIG. 10A: An extract of logarithmically growing HeLa cells stably expressing SCC1-myc was separated by 5-20% sucrose density gradient centrifugation. Proteins from each gradient fraction were analyzed by SDS-PAGE and immunoblotting using antibodies to SCC1, the myc epitope and against the human cohesin subunit SA1. The position of 9S and 14S cohesin complexes is indicated. Both endogenous SCC1 and ectopically expressed SCC1-myc are exclusively found in the fractions containing the 14S cohesin complex.

FIG. 10B: HeLa cells stably expressing SCC1-myc were arrested by double-thymidine treatment and synchronously released into the cell cycle. Samples were taken at the indicated time points and whole cell extracts were analyzed by SDS-PAGE and immunoblotting using antibodies against the myc epitope and the C-terminus of SCC1. SCC1 cleavage products are indicated by arrows. Two exposures of the myc immunoblot are shown to reveal a second SCC1-myc cleavage product of higher electrophoretic mobility that can only be detected in prolonged exposures (bottom panel).

EXAMPLE 11

Figure 11:
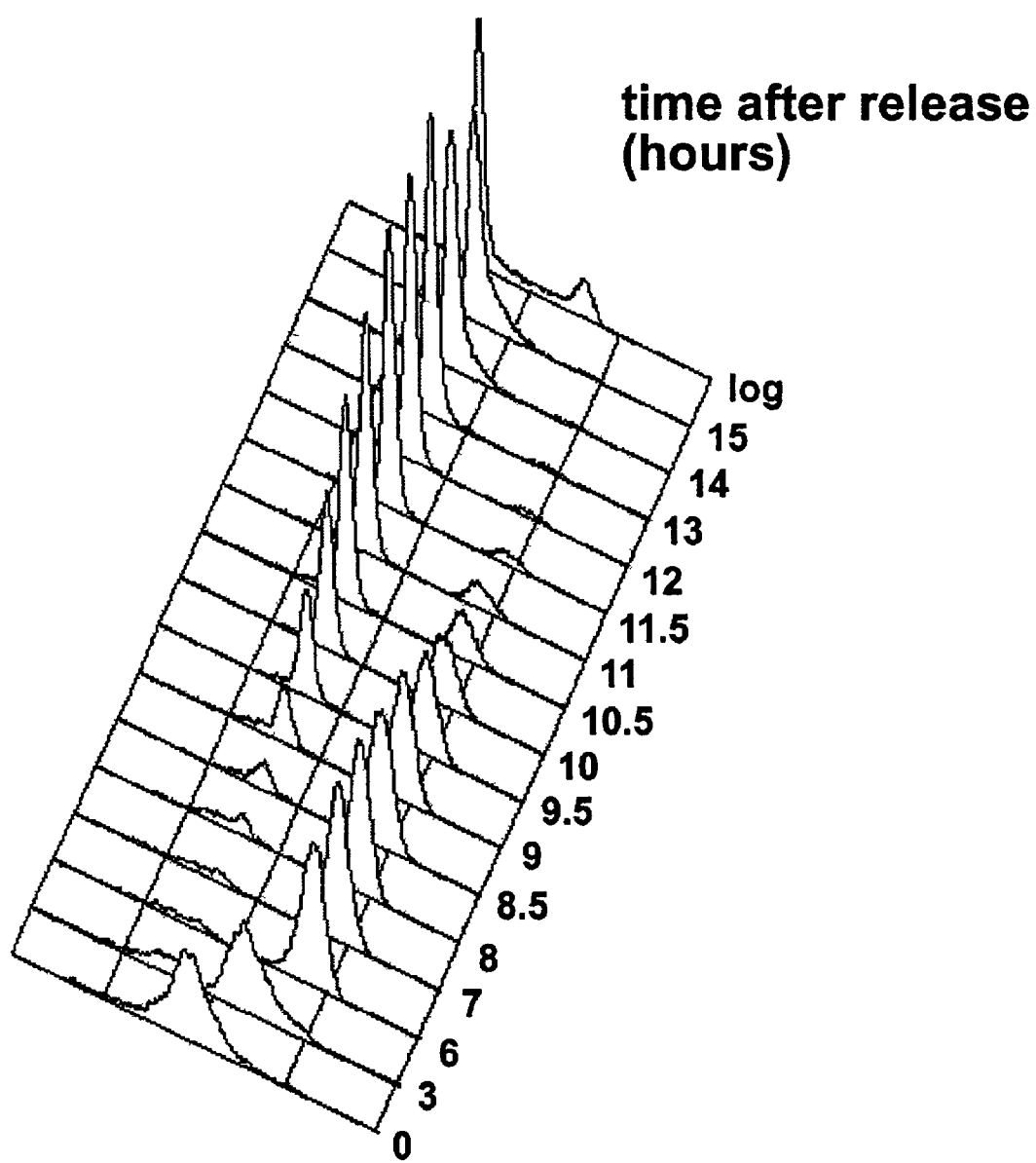
FIG. 11: Human SCC1 is not cleaved in human cells arrested in metaphase by nocodazole treatment
Figure 11:
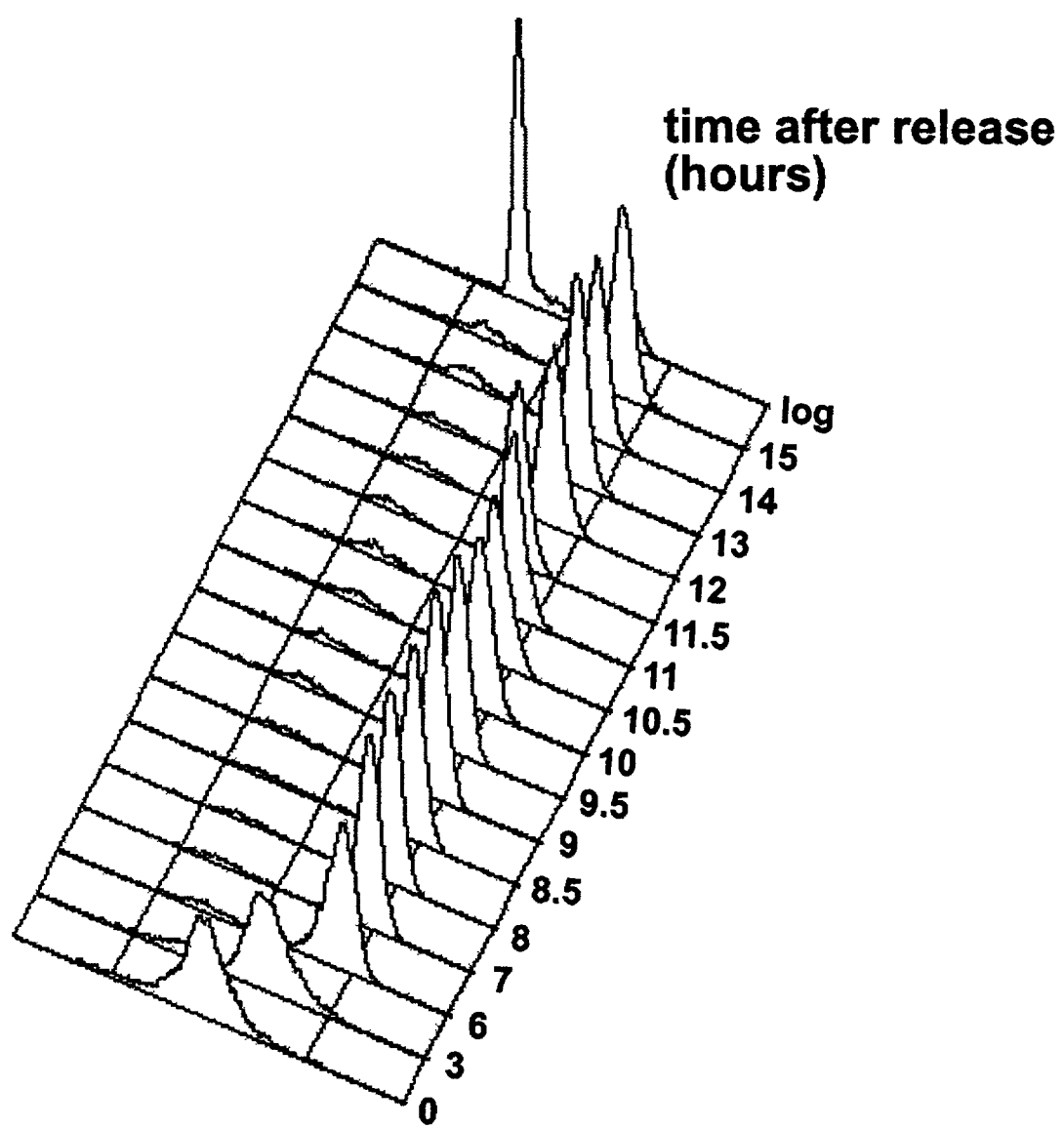
Figure 11:
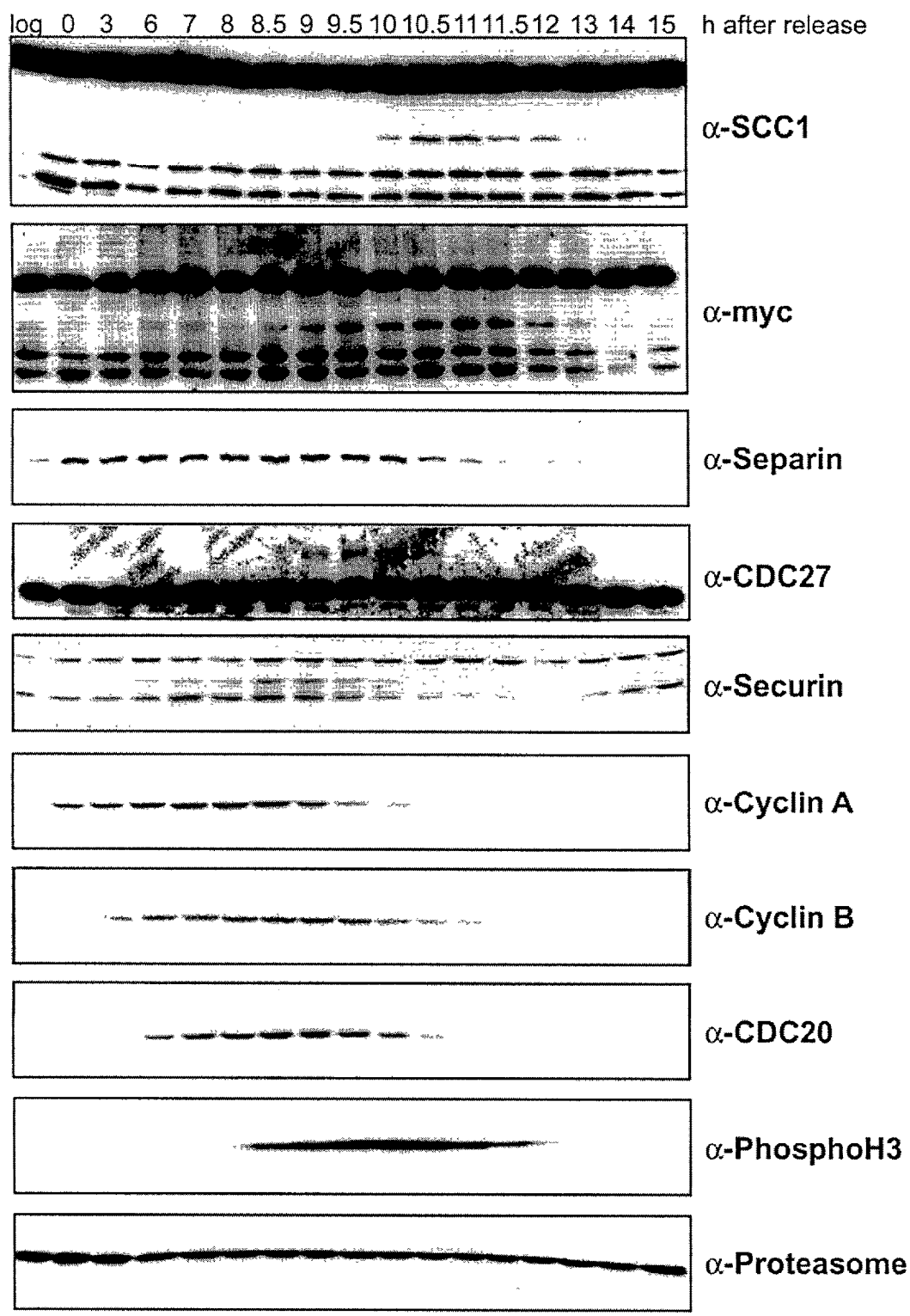
Figure 11:
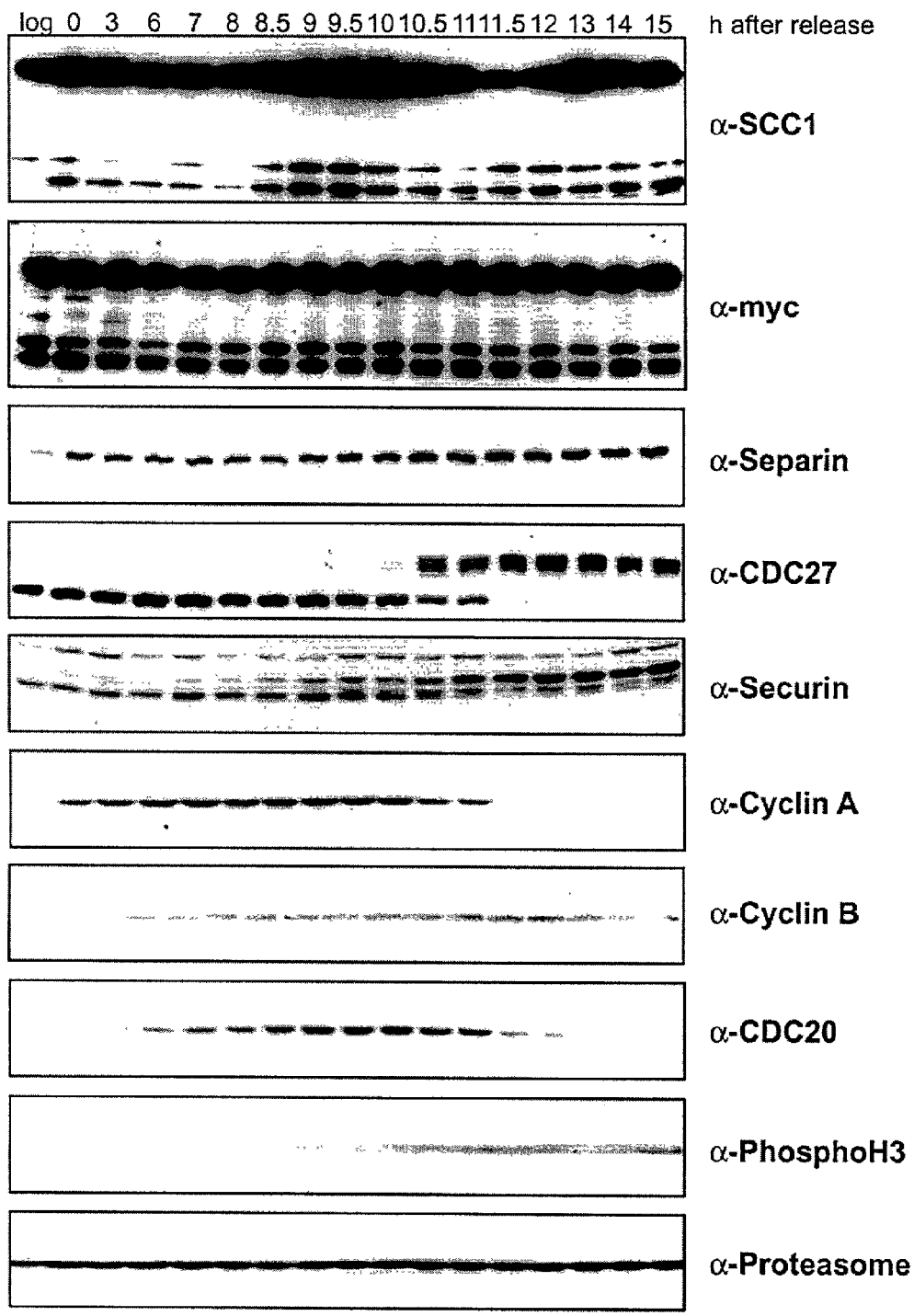

Human SCC1 is not Cleaved in Human Cells Arrested in Metaphase by Nocodazole Treatment HeLa cells stably expressing SCC1-myc were synchronized by double-thymidine treatment and were released into the cell cycle in the presence of either DMSO (results shown in FIGS. 11A and C) or nocodazole dissolved in DMSO (results shown in FIGS. 11B and D). At indicated time points samples were taken. Cells were analyzed by FACsan (FIGS. 11A and B) and by immunoblotting of whole cell extracts using the indicated antibodies (FIGS. 11C and D). Antibodies specific for the C-terminus of SCC1 were used. In addition to the antibodies used in Example 9, an antibody specific for mitotically phosphorylated histone H3 (PhosphoH3) was used as a mitotic marker.

EXAMPLE 12

SCC1 is Cleaved in Anaphase

Figure 12:
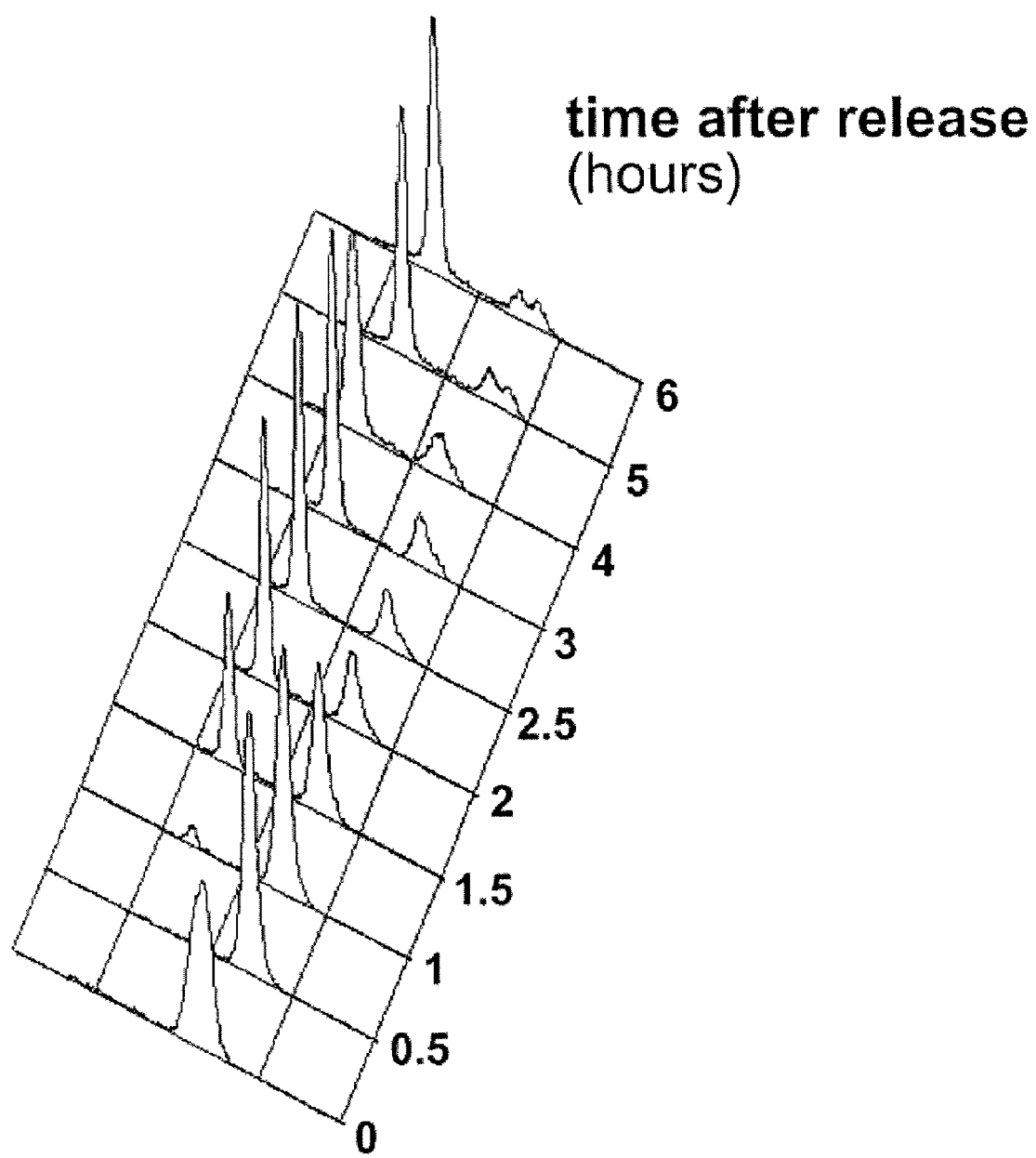
FIG. 12: Human SCC1 is cleaved in anaphase FIG. 13. Human SCC1-myc is cleaved in vitro
Figure 12:
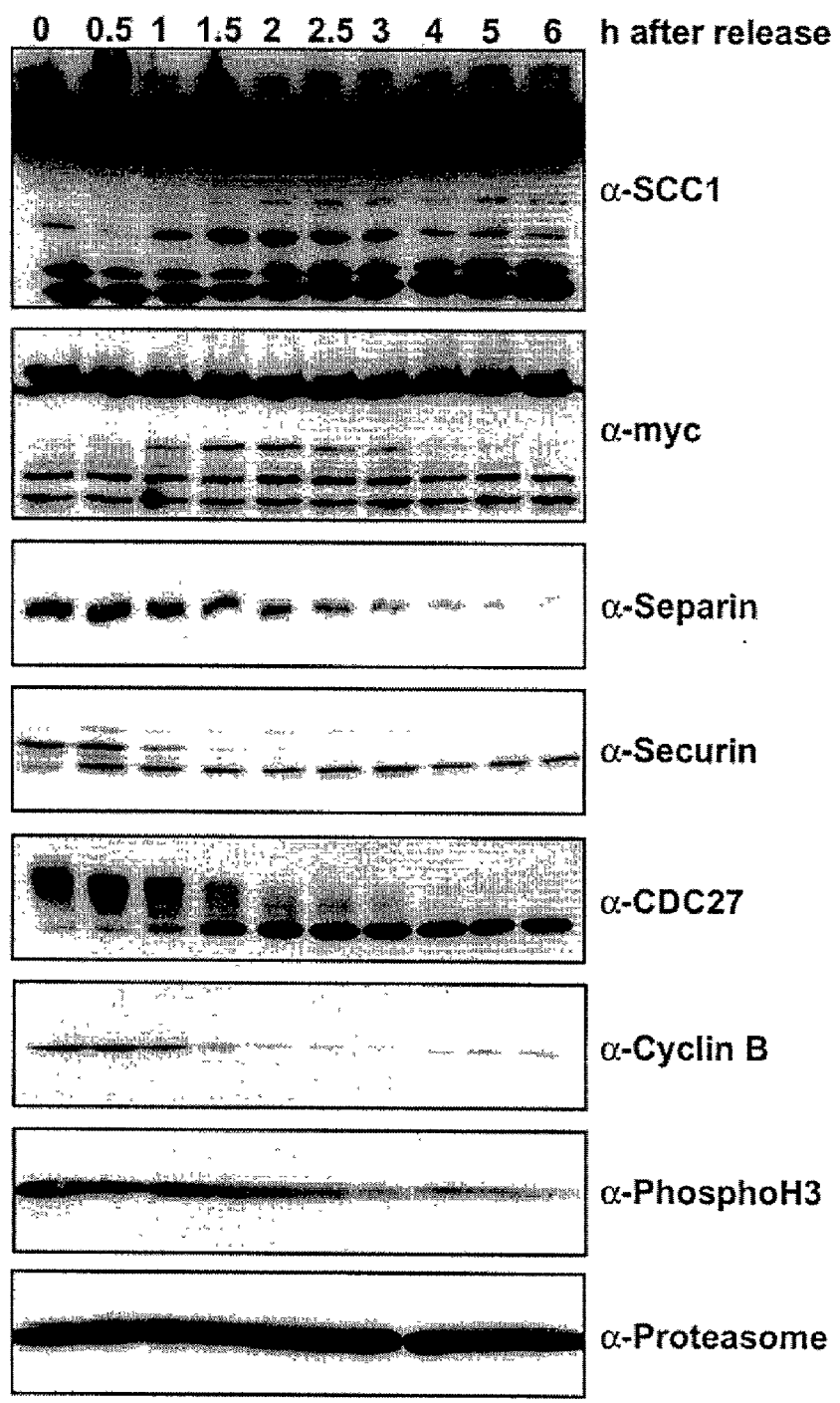

HeLa cells stably expressing SCC1-myc were arrested in metaphase with nocodazole and synchronously released into anaphase. Samples were taken at the indicated time points. Cells were analyzed by FACscan (FIG. 12A) and by immunoblotting of whole cell extracts using the indicated antibodies (FIG. 12B). Antibodies specific for the C-terminus of SCC1 were used.

EXAMPLE 13

SCC1-myc is Cleaved In Vitro

Figure 13:
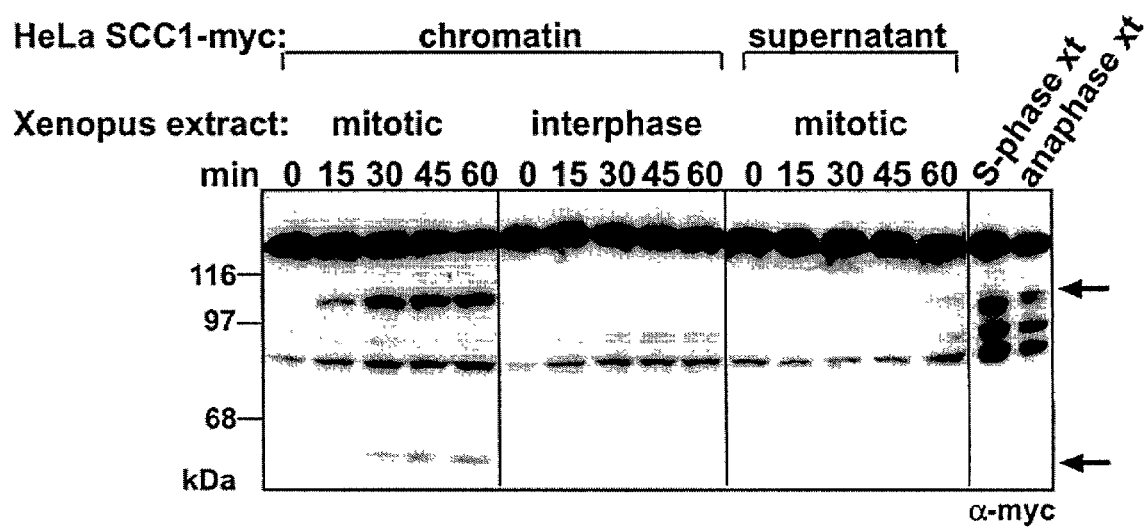

Chromatin and supernatant fractions were isolated by differential centrifugation from nocodazole-arrested HeLa cells stably expressing SCC1-myc. The chromatin fraction was incubated in mitotic and interphase *Xenopus* egg extracts and the supernatant fraction in mitotic *Xenopus* egg extract. Samples were taken at the time points indicated in FIG. 13 and analyzed by SDS-PAGE and immunoblotting using antibodies to the myc epitope. Whole cell extracts from SCC1-myc expressing HeLa cells in S-phase or in anaphase (obtained by release from a double-thymidine arrest for 6 and 11.5 hours, respectively) were analyzed side by side. Cleavage products of SCC1-myc that are specifically formed in mitotic *Xenopus* extracts are indicated by arrows.

EXAMPLE 14

Mapping of the N-Terminal Cleavage Site of Human SCC1

Truncated versions of the human SCC1 cDNA were generated by PCR and transcribed and translated in vitro. The $^{35}$S-labeled in vitro translation products ($^{35}$S-IVT) were analyzed by immunoblotting with SCC1 antibodies (top panels) and by phosphorimaging (bottom panels). N-terminal deletion mutants were analyzed by immunoblotting with antibodies specific for the C-terminus of SCC1 (FIG. 14, left panels) and C-terminal deletion mutants were analyzed with antibodies specific for the N-terminus of SCC1 (FIG. 14, right panels). Extracts from SCC1-myc expressing HeLa cells in anaphase or in G1 (obtained by release from a double-thymidine arrest) were analyzed side by side. The SCC1 cleavage products detected in HeLa extracts are indicated by arrows.

REFERENCES

Ambrose W P, et al., (1998), *Anal Biochem*, October 15, 263(2): 150-7

Brown A M, et al., (1994), *Anal Biochem*, February 15, 217 (1): 139-47

Cai J, et al., (1996): Reconstitution of human replication factor C from its five subunits in baculovirus-infected insect cells. *Proc. Natl. Acad. Sci. U.S.A.* 93, 12896-12901

Cerretani M, et al., (1999), *Anal Biochem*, January 15, 266(2): 192-7

Ciosk R, Zachariae W, Michaelis C, Shevchenko A, Mann M, and Nasmyth K (1998): An ESP1/PDS1 complex regulates loss of sister chromatid cohesion at the metaphase to anaphase transition in yeast. *Cell* 93, 1067-1076

Cohen-Fix O, Peters J-M, Kirschner M W, and Koshland D (1996): Anaphase initiation is Sacharomyces cervisiae is controlled by the APC-dependent degradation of the anaphase inhibitor Pds1p. *Genes Dev* 10, 3081-3093

Dougherty W G, Cary S M and Dawn Parks T (1989): Molecular Genetic Analysis of a Plant Virus Polyprotein Cleavage Site: A Model. Virology 171, 356-364

Dominguez A, Ramos-Morales F, Romero F, Rios R M, Dreyfus F, Tortolero M and Pintor-Toro J A (1998): hpttg, a human homologue of rat pttg, is overexpressed in hematopoietic neoplasms. Evidence for a transcrptional activation function of hPTTG. *Oncogene* 17: 2187-2193

Epstein C B, and Cross F R (1992) CLB5: a novel cyclin from budding yeast with a role in S-phase. *Genes Dev.* 6, 1695-1706

Faleiro L, Kobayashi R, Fearnhead H, and Lazebnik Y (1997): Multiple species of CPP32 and Mch2 are the major active caspases present in apoptotic cells. *EMBO J.* 16, 2271-2281

Funabiki H, et al., (1996): *Cut*2 proteolysis required for sister-chromatid separation in fission yeast. *Nature* 381, 438-441

Gershkovich, A. A. and Kholodovych, V. V. (1996), J Biochem Biophys Meth 33, 135

Gietz R D and Sugino A (1988): New yeast-*Escherichia coli* shuttle vectors constructed with in vitro mutagenized yeast genes lacking six-base pair restriction sites. *Gene* 74, 527-534

Gray N M, et al., (1994), *Anal Biochem,* 216(1): 89-96

Guthrie, C. and Fink, G. R, editors (1991): Guide to Yeast Genetics and Molecular Biology, Methods in Enzymology, Volume 194, Academic Press, Inc., U.S.A.

Hayden J H, Bowser S S, and Rieder C L (1990): Kinetochores capture astral microtubules during chromosome attachment to the mitotic spindle: direct visualization in live newt lung cells. *J. Cell Biol.* 3, 1039-1045

Jolley, M. E. (1996), *J Biomol Screening* 1, 33

Kramer E R, Gieffers C, Hölzl G, Hengstschlager M and Peters J M (1998): Activation of the human anaphase-promoting complex by proteins of the CDC10/Fizzy family. *Current Biology* 8: 1207-1210

Kerrebrock A W, Moore D P, Wu J S, and Orr-Weaver T L (1995): Mei-S332, a *Drosophila* protein required for sister chromatid cohesion, can localize to meiotic centromere regions. *Cell* 83, 247-256

Klein F, et al., (1999): A central role for the cohesins in sister chromatid cohesion, formation of axial elements, and recombination during yeast meiosis. *Cell* 98, 91-103

Levine L M, et al., (1997), *Anal Biochem,* April 5, 247(1): 83-8

Liang C, and Stillman B (1997): Persistent initiation of DNA replication and chromatin-bound MCM proteins during the cell cycle in cdc6 mutants. *Genes Dev* 11, 3375-3386

Lim H H, Goh P-Y, and Surana U (1998): Cdc20 is essential for the cyclosome-mediated proteolysis of both Pds1 and Clb2 during M phase in budding yeast. *Curr. Biol.* 8, 231-234

Losada A, Hirano M, and Hirano T (1998): Identification of *Xenopus* SMC protein complexes required for sister chromatid cohesion. *Genes Dev* 12, 1003-1012

Matayoshi, E. D. (1990), Science 247, 954

McKay M J, et al., (1996): Sequence conservation of the rad21 *Schizosaccharomyces* pompe DNA double-strand break repair gene in human and mouse. *Genomics* 36, 305-315

McGrew J T, Goetsch L, Byers B, and Baum P (1992): Requirement for ESP1 in the nuclear division of *S. cerevisiae. Mol. Biol. Cell* 3, 1443-1454

Merdes A, and De Mey J (1990): The mechanism of kinetochore-spindle attachment and polewards movement analyzed in PtK2 cells at the prophase-prometaphase transition. *Eur. J. Cell Biol.* 53, 313-325

Michaelis C, Ciosk R, and Nasmyth K (1997): Cohesins: Chromosomal proteins that prevent premature separation of sister chromatids. *Cell* 91, 35-45

Miyazaki W Y, and Orr-Weaver T L (1994): Sister chromatid cohesion in mitosis and meiosis. Annu. Rev. Genet. 28, 167-187

Moore D P, Page A W, Tang T T L, Kerrebrock A W, and Orr-Weaver T L (1998): The cohesion protein Mei-*S*322 localizes to condensed meiotic and mitotic centromeres until sister chromatids separate. *J. Cell Biol.* 140, 1003-1012

Murray A W (1991): Cell cycle extracts. Methods In cell biology 36, 581-605

Murray M G, et al., (1993), *Gene,* November 30, 134(1): 123-8

Nagase T, Seki N, Ishikawa K, Tanaka A, and Nomura N (1996): Prediction of the coding sequences of unidentified human genes. V. The coding sequences of 40 new genes (KIAA0161-KIAA0200) deduced by analysis of cDNA clones from human cell line KG-1. DNA Res 3, 17-24

Nicholson D W, et al., (1995): Identification and inhibition of the ICE/CED-3 protease necessary for mammalian apoptosis. Nature 376, 37-43

Peters J-M (1998): SCF and APC the Yin and Yan of cell cycle regulated proteolysis. *Curr. Op. Cell Biol.* 10, 759-768

Remington's Pharmacuetical Sciences, 1980, Mack Publ. Co. Easton, Pa., Osol (ed.)

Rieder C L, and Salmon E D (1998): The vertebrate cell kinetochore and its roles during mitosis. *Trends Cell. Biol.* 8, 310-318

Rose M D, Winston F, and Hieter P (1990): Laboratory course manual for methods in Yeast Genetics (Cold Spring Harbor Laboratory Press, Cold Spring Harbor, N.Y.)

Sarubbi E, et al., (1991), *FEBS Lett*, February 25, 279(2): 265-9

Singh J, et al., (1996), *Bioorg Med Chem,* 4(5): 639-43

Stebbins J. and Debouck C., (1997), *Anal Biochem*, June 1, 248(2): 246-50

Taliani M, et al., (1996), *Anal Biochem,* August 15, 240(1): 60-7

Uhlmann F, and Nasmyth K (1998): Cohesion between sister chromatids must be established during DNA replication. *Curr. Biol.* 8, 1095-1101

Zou H, McGerry T J, Bernal T, Kirschner M W (1999): Identification of a vertebrate sister-chromatid separation inhibitor involved in transformation and tumorigenesis. Science 285:418-422

The invention claimed is:

1. A method for identifying a compound that has the activity of inhibiting sister chromatid separation in eukaryotic cells, said method comprising:

(a) incubating with a test compound a separin in the presence of a separin substrate, wherein said substrate is a peptide or polypeptide comprising an amino acid sequence EXXR (SEQ ID NO:3), wherein X is any amino acid, and the substrate is capable of being cleaved by the separin; and (b) determining the inhibiting effect of the test compound on the proteolytic activity of the separin, wherein a compound determined in (b) to inhibit the proteolytic activity of the separin has the activity of inhibiting sister chromatid separation in eukaryotic cells.

2. The method of claim 1, wherein said eukaryotic cell is an animal cell.

3. The method of claim 1, which is high-throughput.

4. The method of claim 1, wherein said separin is recombinant.

5. The method of claim 1, wherein said separin is human separin.

6. The method of claim 1, wherein said substrate is a protein recombinantly produced in baculovirus in the presence of a phosphatase inhibitor.

7. The method of claim 1, wherein said substrate is human SCC1, or a fragment thereof that can be cleaved by separin or having a separin cleavage site.

8. The method of claim 7, wherein said substrate is a polypeptide comprising the amino acid sequence of SEQ ID NO:1, or a fragment thereof that can be cleaved by separin or having a separin cleavage site.

9. The method of claim 1, wherein said substrate comprises a label which generates a detectable signal proportional to the amount of the cleavage product of the proteolytic activity, and wherein the signal is measured in the presence and in the absence of the test compound.

10. The method of claim 9, wherein said label is fluorescent.

11. The method of claim 1, wherein said substrate is human SCC1.

12. The method of claim 7, wherein said substrate is a polypeptide comprising the amino acid sequence of SEQ ID NO:1.

* * * * *

SEQUENCE LISTING

<160> NUMBER OF SEQ ID NOS: 3

<210> SEQ ID NO 1
<211> LENGTH: 18
<212> TYPE: PRT
<213> ORGANISM: Homo sapiens

<400> SEQUENCE: 1

Met Asp Asp Arg Glu Ile Met Arg Glu Gly Ser Ala Phe Glu Asp Asp
1               5                   10                  15

Asp Met

<210> SEQ ID NO 2

```
-continued

<211> LENGTH: 7
<212> TYPE: PRT
<213> ORGANISM: Artificial Sequence
<220> FEATURE:
<223> OTHER INFORMATION: TEV protease cleavage site

<400> SEQUENCE: 2

Glu Asn Leu Tyr Phe Gln Gly
1               5

<210> SEQ ID NO 3
<211> LENGTH: 4
<212> TYPE: PRT
<213> ORGANISM: Artificial Sequence
<220> FEATURE:
<223> OTHER INFORMATION: Synthetic sequence used as a separin substrate
<220> FEATURE:
<221> NAME/KEY: MISC_FEATURE
<222> LOCATION: (2)..(3)
<223> OTHER INFORMATION: Xaa can be any amino acid

<400> SEQUENCE: 3

Glu Xaa Xaa Arg
1
```